United States Patent
Cao et al.

(10) Patent No.: US 10,502,843 B2
(45) Date of Patent: *Dec. 10, 2019

(54) SEMICONDUCTOR X-RAY DETECTOR

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 95 days.

This patent is subject to a terminal disclaimer.

(21) Appl. No.: 15/866,928

(22) Filed: Jan. 10, 2018

(65) Prior Publication Data

US 2018/0156927 A1    Jun. 7, 2018

Related U.S. Application Data

(63) Continuation of application No. 15/122,456, filed as application No. PCT/CN2015/075941 on Apr. 7, 2015, now Pat. No. 10,007,009.

(51) Int. Cl.
| | | |
|---|---|---|
| *G01T 1/24* | (2006.01) | |
| *A61B 6/03* | (2006.01) | |
| *G01V 5/00* | (2006.01) | |
| *G21K 7/00* | (2006.01) | |

(52) U.S. Cl.
CPC ............. *G01T 1/247* (2013.01); *A61B 6/032* (2013.01); *G01V 5/0025* (2013.01); *G21K 7/00* (2013.01)

(58) Field of Classification Search
CPC ....... G01T 1/247; A61B 6/032; G01V 5/0025; G21K 7/00
See application file for complete search history.

(56) References Cited

U.S. PATENT DOCUMENTS

| | | | |
|---|---|---|---|
| 5,635,718 A | 6/1997 | Depuydt et al. | |
| 10,007,009 B2* | 6/2018 | Cao | ............ G01T 1/247 |
| 2010/0225837 A1 | 9/2010 | Seki et al. | |
| 2011/0121191 A1 | 5/2011 | Kappler et al. | |
| 2012/0223241 A1 | 9/2012 | Kim et al. | |
| 2014/0334600 A1 | 11/2014 | Lee et al. | |

FOREIGN PATENT DOCUMENTS

| | | |
|---|---|---|
| CN | 101529274 B | 7/2012 |
| CN | 102655159 B | 9/2016 |
| DE | 102012215818 A1 | 3/2014 |

(Continued)

*Primary Examiner* — Courtney D Thomas
(74) *Attorney, Agent, or Firm* — IPro, PLLC; Qian Gu

(57) ABSTRACT

Disclosed herein is an apparatus suitable for detecting X-ray, comprising: an X-ray absorption layer comprising an electrode; an electronics layer, the electronics layer comprising: a substrate having a first surface and a second surface, an electronics system in or on the substrate, an electric contact on the first surface, a via, and a transmission line on the second surface; wherein the via extends from the first surface to the second surface; wherein the electrode is electrically connected to the electric contact; wherein the electronics system is electrically connected to the electric contact and the transmission line through the via.

27 Claims, 27 Drawing Sheets

(56) References Cited

FOREIGN PATENT DOCUMENTS

| | | | |
|---|---|---|---|
| JP | H05264738 | A | 10/1993 |
| JP | H10506230 | A | 6/1998 |
| JP | 2000504410 | A | 4/2000 |
| JP | 2004265883 | A | 9/2004 |
| JP | 2004362905 | A | 12/2004 |
| JP | 2009503506 | A | 1/2009 |
| JP | 2009078143 | A | 4/2009 |
| JP | 2010507797 | A | 3/2010 |
| JP | 2010538293 | A | 12/2010 |
| JP | 4734224 | B2 | 7/2011 |
| JP | 2012118060 | A | 6/2012 |
| JP | 2012185159 | A | 9/2012 |
| JP | 2013085966 | A | 5/2013 |
| JP | 2014059155 | A | 4/2014 |
| JP | 2015011018 | A | 1/2015 |
| JP | 2015021866 | A | 2/2015 |
| KR | 101410736 | B1 | 6/2014 |
| KR | 20150032754 | A | 3/2015 |
| WO | 1997026677 | | 7/1997 |
| WO | 2008050283 | A3 | 7/2008 |
| WO | 2013057803 | A1 | 4/2013 |
| WO | 2014121097 | A1 | 8/2014 |
| WO | 2015040703 | A1 | 3/2015 |

\* cited by examiner

Fig. 2

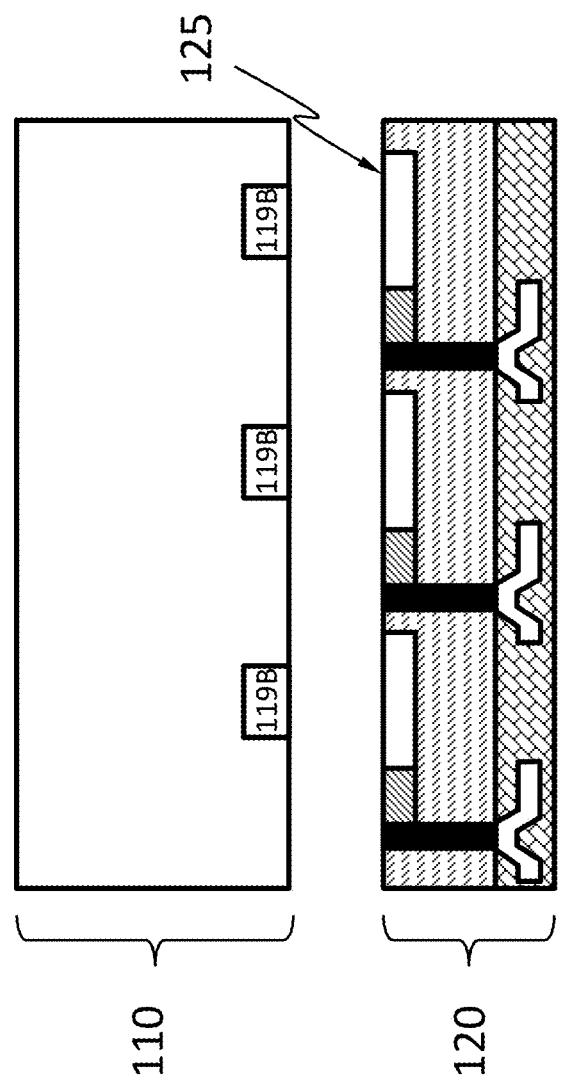

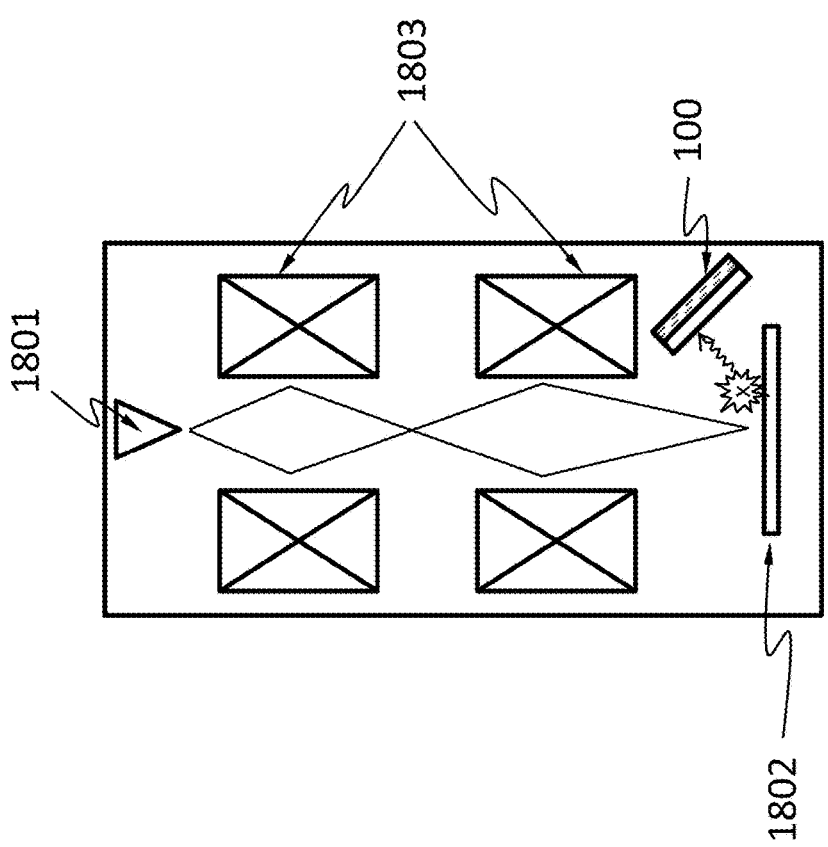

SEMICONDUCTOR X-RAY DETECTOR

TECHNICAL FIELD

The disclosure herein relates to X-ray detectors, particularly relates to semiconductor X-ray detectors.

BACKGROUND

X-ray detectors may be devices used to measure the flux, spatial distribution, spectrum or other properties of X-rays.

X-ray detectors may be used for many applications. One important application is imaging. X-ray imaging is a radiography technique and can be used to reveal the internal structure of a non-uniformly composed and opaque object such as the human body.

Early X-ray detectors for imaging include photographic plates and photographic films. A photographic plate may be a glass plate with a coating of light-sensitive emulsion. Although photographic plates were replaced by photographic films, they may still be used in special situations due to the superior quality they offer and their extreme stability. A photographic film may be a plastic film (e.g., a strip or sheet) with a coating of light-sensitive emulsion.

In the 1980s, photostimulable phosphor plates (PSP plates) became available. A PSP plate may contain a phosphor material with color centers in its lattice. When the PSP plate is exposed to X-ray, electrons excited by X-ray are trapped in the color centers until they are stimulated by a laser beam scanning over the plate surface. As the plate is scanned by laser, trapped excited electrons give off light, which is collected by a photomultiplier tube. The collected light is converted into a digital image. In contrast to photographic plates and photographic films, PSP plates can be reused.

Another kind of X-ray detectors are X-ray image intensifiers. Components of an X-ray image intensifier are usually sealed in a vacuum. In contrast to photographic plates, photographic films, and PSP plates, X-ray image intensifiers may produce real-time images, i.e., do not require post-exposure processing to produce images. X-ray first hits an input phosphor (e.g., cesium iodide) and is converted to visible light. The visible light then hits a photocathode (e.g., a thin metal layer containing cesium and antimony compounds) and causes emission of electrons. The number of emitted electrons is proportional to the intensity of the incident X-ray. The emitted electrons are projected, through electron optics, onto an output phosphor and cause the output phosphor to produce a visible-light image.

Scintillators operate somewhat similarly to X-ray image intensifiers in that scintillators (e.g., sodium iodide) absorb X-ray and emit visible light, which can then be detected by a suitable image sensor for visible light. In scintillators, the visible light spreads and scatters in all directions and thus reduces spatial resolution. Reducing the scintillator thickness helps to improve the spatial resolution but also reduces absorption of X-ray. A scintillator thus has to strike a compromise between absorption efficiency and resolution.

Semiconductor X-ray detectors largely overcome this problem by direct conversion of X-ray into electric signals. A semiconductor X-ray detector may include a semiconductor layer that absorbs X-ray in wavelengths of interest. When an X-ray photon is absorbed in the semiconductor layer, multiple charge carriers (e.g., electrons and holes) are generated and swept under an electric field towards electrical contacts on the semiconductor layer. Cumbersome heat management required in currently available semiconductor X-ray detectors (e.g., Medipix) can make a detector with a large area and a large number of pixels difficult or impossible to produce.

SUMMARY

Disclosed herein is an apparatus suitable for detecting x-ray, comprising: an X-ray absorption layer comprising an electrode; an electronics layer, the electronics layer comprising: a substrate having a first surface and a second surface, an electronics system in or on the substrate, an electric contact on the first surface, a via, and a redistribution layer (RDL) on the second surface; wherein the RDL comprises a transmission line; wherein the via extends from the first surface to the second surface; wherein the electrode is electrically connected to the electric contact; wherein the electronics system is electrically connected to the electric contact and the transmission line through the via.

According to an embodiment, the substrate has a thickness of 200 µm or less.

According to an embodiment, the electronics system comprises: a first voltage comparator configured to compare a voltage of the electrode to a first threshold; a second voltage comparator configured to compare the voltage to a second threshold; a counter configured to register a number of X-ray photons reaching the X-ray absorption layer; a controller; wherein the controller is configured to start a time delay from a time at which the first voltage comparator determines that an absolute value of the voltage equals or exceeds an absolute value of the first threshold; wherein the controller is configured to activate the second voltage comparator during the time delay; wherein the controller is configured to cause the number registered by the counter to increase by one, if the second voltage comparator determines that an absolute value of the voltage equals or exceeds an absolute value of the second threshold.

According to an embodiment, the controller is configured to deactivate the first voltage comparator at a beginning of the time delay.

According to an embodiment, the controller is configured to deactivate the second voltage comparator at expiration of the time delay or at a time when the second voltage comparator determines that the absolute value of the voltage equals or exceeds the absolute value of the second threshold, or a time in between.

According to an embodiment, the apparatus further comprises a capacitor module electrically connected to the electrode, wherein the capacitor module is configured to collect charge carriers from the electrode.

According to an embodiment, the controller is configured to activate the second voltage comparator at a beginning or expiration of the time delay.

According to an embodiment, the apparatus further comprises a voltmeter, wherein the controller is configured to cause the voltmeter to measure the voltage upon expiration of the time delay.

According to an embodiment, the controller is configured to determine an X-ray photon energy based on a value of the voltage measured upon expiration of the time delay.

According to an embodiment, the controller is configured to connect the electrode to an electrical ground.

According to an embodiment, a rate of change of the voltage is substantially zero at expiration of the time delay.

According to an embodiment, a rate of change of the voltage is substantially non-zero at expiration of the time delay.

According to an embodiment, the X-ray absorption layer comprises a diode.

According to an embodiment, the X-ray absorption layer comprises silicon, germanium, GaAs, CdTe, CdZnTe, or a combination thereof.

According to an embodiment, the apparatus does not comprise a scintillator.

According to an embodiment, the apparatus comprises an array of pixels.

Disclosed herein is a system comprising the apparatus disclosed herein and an X-ray source, wherein the system is configured to perform X-ray radiography on human chest or abdomen.

Disclosed herein is a system comprising the apparatus disclosed herein and an X-ray source, wherein the system is configured to perform X-ray radiography on human mouth.

Disclosed herein is a cargo scanning or non-intrusive inspection (NII) system, comprising the apparatus disclosed herein and an X-ray source, wherein the cargo scanning or non-intrusive inspection (NII) system is configured to form an image using backscattered X-ray.

Disclosed herein is a cargo scanning or non-intrusive inspection (NII) system, comprising the apparatus disclosed herein and an X-ray source, wherein the cargo scanning or non-intrusive inspection (NII) system is configured to form an image using X-ray transmitted through an object inspected.

Disclosed herein is a full-body scanner system comprising the apparatus disclosed herein and an X-ray source.

Disclosed herein is an X-ray computed tomography (X-ray CT) system comprising the apparatus disclosed herein and an X-ray source.

Disclosed herein is an electron microscope comprising the apparatus disclosed herein, an electron source and an electronic optical system.

Disclosed herein is a system comprising the apparatus disclosed herein, wherein the system is an X-ray telescope, or an X-ray microscopy, or wherein the system is configured to perform mammography, industrial defect detection, microradiography, casting inspection, weld inspection, or digital subtraction angiography.

Disclosed herein is a method comprising: obtaining an X-ray absorption layer comprising an electrode; obtaining an electronics layer, the electronics layer comprising: a substrate having a first surface and a second surface, an electronics system in or on the substrate, an electric contact on the first surface, a via, and a redistribution layer (RDL) on the second surface; bonding the X-ray absorption layer and the electronics layer such that the electrode is electrically connected to the electric contact; wherein the RDL comprises a transmission line; wherein the via extends from the first surface to the second surface; wherein the electronics system is electrically connected to the electric contact and the transmission line through the via.

BRIEF DESCRIPTION OF FIGURES

FIG. 2 shows an exemplary top view of a portion of the detector in FIG. 1A, according to an embodiment.

FIG. 4A schematically shows direct bonding between an X-ray absorption layer and an electronic layer.

FIG. 19 schematically shows an electron microscope comprising the semiconductor X-ray detector described herein, according to an embodiment.

DETAILED DESCRIPTION

Figure 1A:
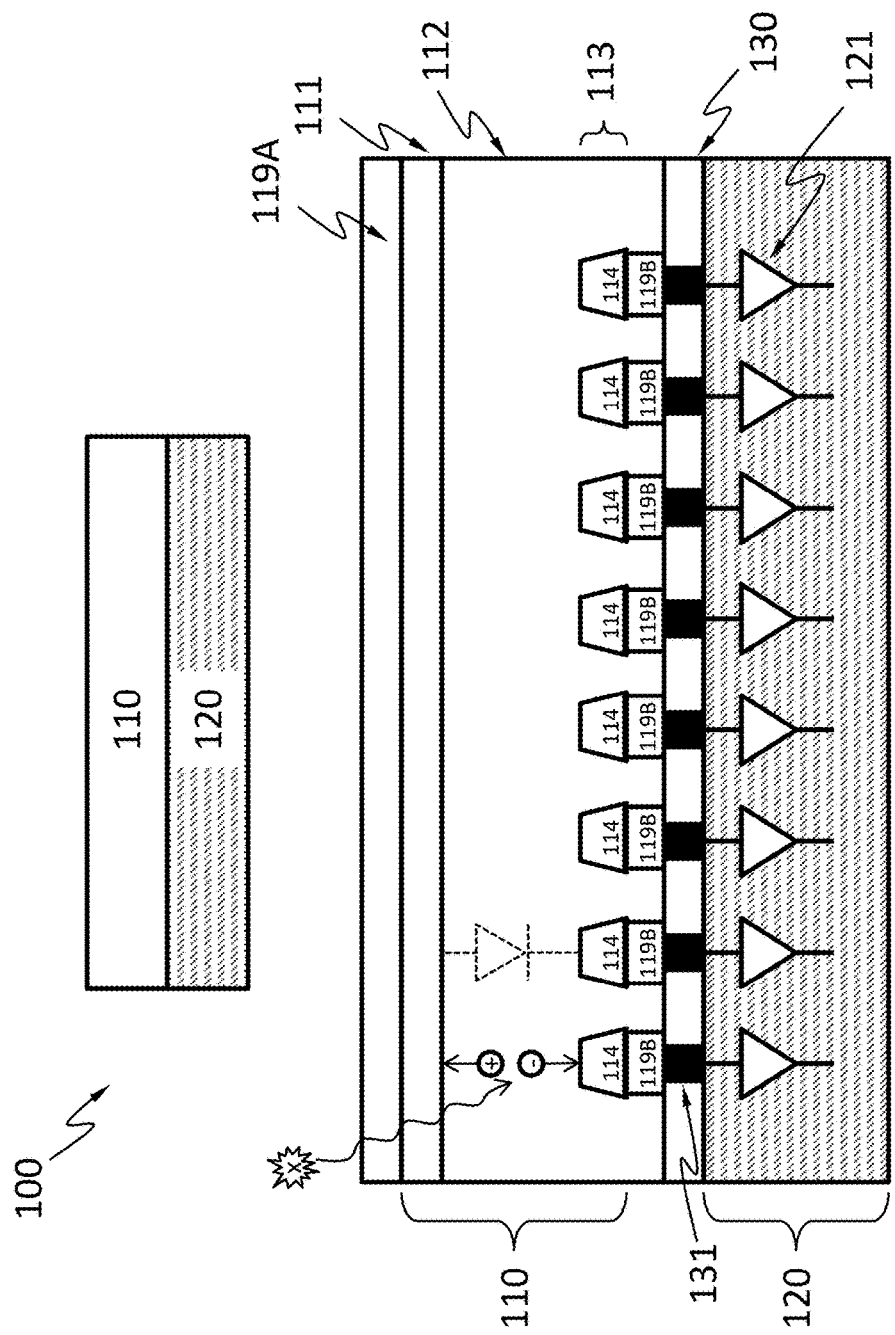
FIG. 1A schematically shows a semiconductor X-ray detector, according to an embodiment.

FIG. 1A schematically shows a semiconductor X-ray detector 100, according an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest. The X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 1A, each of the discrete regions 114 of the second doped region 113 forms a diode with the first doped region 111 and the optional intrinsic region 112. Namely, in the example in FIG. 1A, the X-ray absorption layer 110 has a plurality of diodes having the first doped region 111 as a shared electrode. The first doped region 111 may also have discrete portions.

Figure 1B:
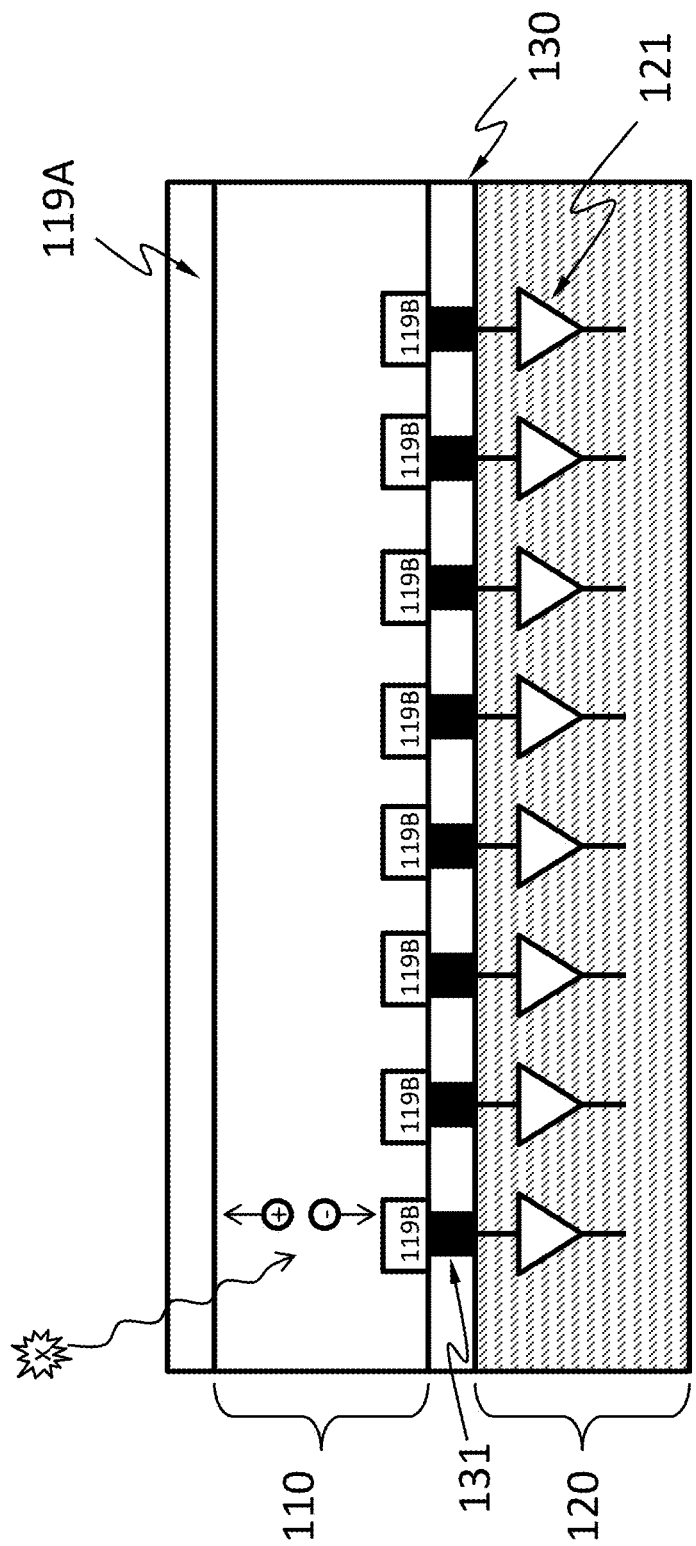
FIG. 1B shows a semiconductor X-ray detector 100, according an embodiment.

FIG. 1B shows a semiconductor X-ray detector 100, according an embodiment. The semiconductor X-ray detector 100 may include an X-ray absorption layer 110 and an electronics layer 120 (e.g., an ASIC) for processing or analyzing electrical signals incident X-ray generates in the X-ray absorption layer 110. In an embodiment, the semiconductor X-ray detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest. The X-ray absorption layer 110 may not include a diode but includes a resistor.

Figure 2:
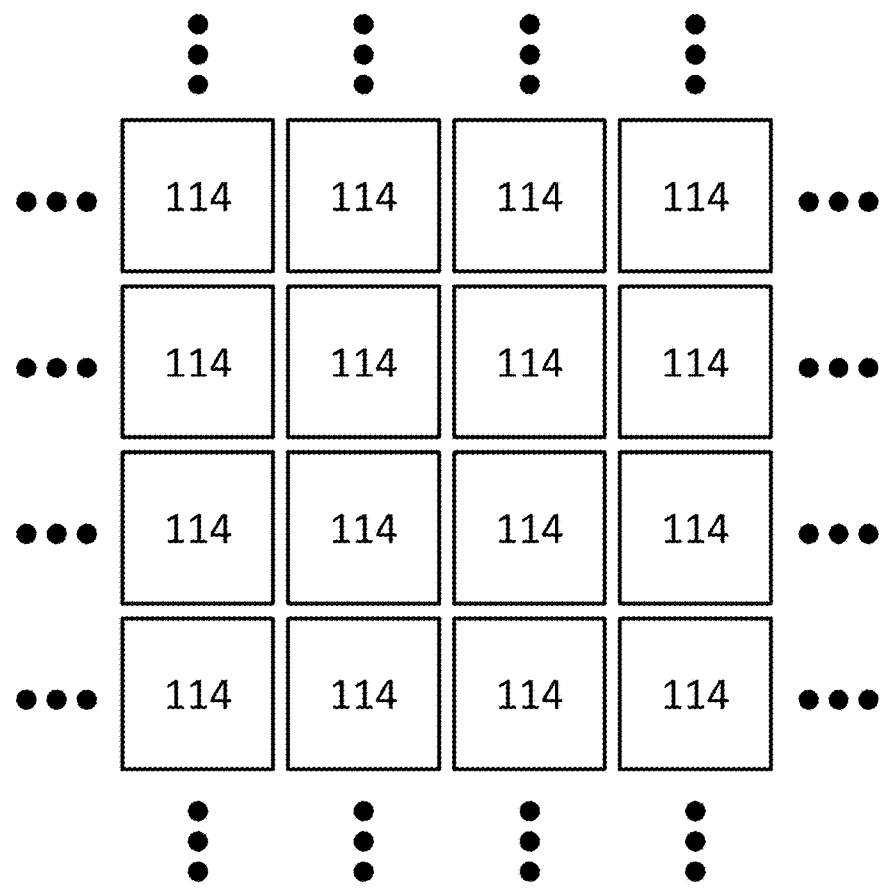

When an X-ray photon hits the X-ray absorption layer 110 including diodes, it may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single X-ray photon are not substantially shared by two different discrete regions 114 ("not substantially shared" here means less than 5%, less than 2% or less than 1% of these charge carriers flow to a different one of the discrete regions 114 than the rest of the charge carriers). In an embodiment, the charge carriers generated by a single X-ray photon can be shared by two different discrete regions 114. FIG. 2 shows an exemplary top view of a portion of the device 100 with a 4-by-4 array of discrete regions 114. Charge carriers generated by an X-ray photon incident around the footprint of one of these discrete regions 114 are not substantially shared with another of these discrete regions 114. The area around a discrete region 114 in which substantially all (more than 95%, more than 98% or more than 99% of) charge carriers generated by an X-ray photon incident therein flow to the discrete region 114 is called a pixel associated with the discrete region 114. Namely, less than 5%, less than 2% or less than 1% of these charge carriers flow beyond the pixel. By measuring the drift current flowing into each of the discrete regions 114, or the rate of change of the voltage of each of the discrete regions 114, the number of X-ray photons absorbed (which relates to the incident X-ray intensity) and/or the energies thereof in the pixels associated with the discrete regions 114 may be determined. Thus, the spatial distribution (e.g., an image) of incident X-ray intensity may be determined by individually measuring the drift current into each one of an array of discrete regions 114 or measuring the rate of change of the voltage of each one of an array of discrete regions 114. The pixels may be organized in any suitable array, such as, a square array, a triangular array and a honeycomb array. The pixels may have any suitable shape, such as, circular, triangular, square, rectangular, and hexagonal. The pixels may be individually addressable.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single X-ray photon are not substantially shared by two different discrete portions of the electrical contact 119B ("not substantially shared" here means less than 5%, less than 2% or less than 1% of these charge carriers flow to a different one of the discrete portions than the rest of the charge carriers). In an embodiment, the charge carriers generated by a single X-ray photon can be shared by two different discrete portions of the electrical contact 119B. Charge carriers generated by an X-ray photon incident around the footprint of one of these discrete portions of the electrical contact 119B are not substantially shared with another of these discrete portions of the electrical contact 119B. The area around a discrete portion of the electrical contact 119B in which substantially all (more than 95%, more than 98% or more than 99% of) charge carriers generated by an X-ray photon incident therein flow to the discrete portion of the electrical contact 119B is called a pixel associated with the discrete portion of the electrical contact 119B. Namely, less than 5%, less than 2% or less than 1% of these charge carriers flow beyond the pixel associated with the one discrete portion of the electrical contact 119B. By measuring the drift current flowing into each of the discrete portion of the electrical contact 119B, or the rate of change of the voltage of each of the discrete portions of the electrical contact 119B, the number of X-ray photons absorbed (which relates to the incident X-ray intensity) and/or the energies thereof in the pixels associated with of the discrete portions of the electrical contact 119B may be determined. Thus, the spatial distribution (e.g., an image) of incident X-ray intensity may be determined by individually measuring the drift current into each one of an array of discrete portions of the electrical contact 119B or measuring the rate of change of the voltage of each one of an array of discrete portions of the electrical contact 119B. The pixels may be organized in any suitable array, such as, a square array, a triangular array and a honeycomb array. The pixels may have any suitable shape, such as, circular, triangular, square, rectangular, and hexangular. The pixels may be individually addressable.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 3A:
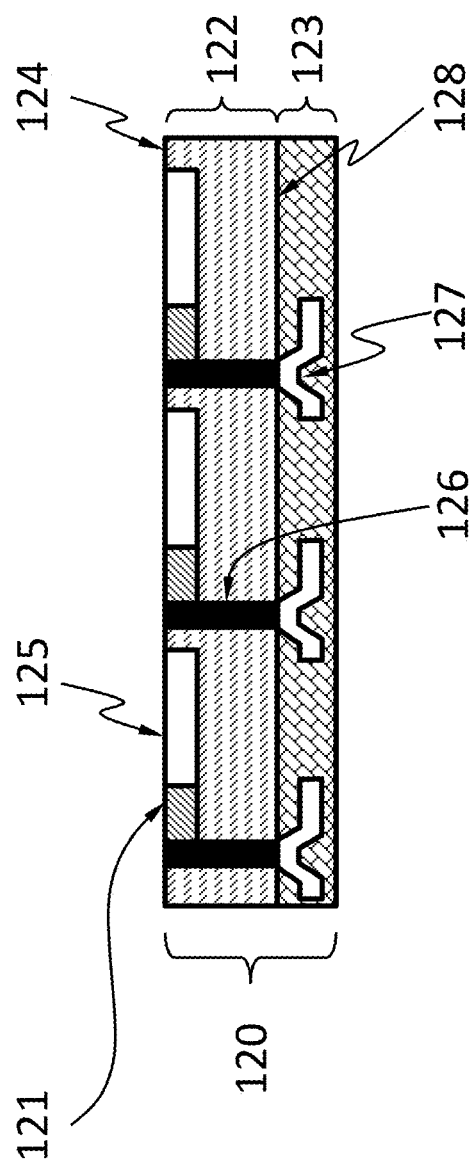
FIG. 3A schematically shows the electronics layer 120 according to an embodiment.

FIG. 3A schematically shows the electronics layer 120 according to an embodiment. The electronic layer 120 comprises a substrate 122 having a first surface 124 and a second surface 128. A "surface" as used herein is not necessarily exposed, but can be buried wholly or partially. The electronic layer 120 comprises one or more electric contacts 125 on the first surface 124. The one or more electric contacts 125 may be configured to be electrically connected to one or more electrodes of the X-ray absorption layer 110. The electronics system 121 may be in or on the substrate 122. The electronic layer 120 comprises one or more vias 126 extending from the first surface 124 to the second surface 128. The electronic layer 120 comprises a redistribution layer (RDL) 123 on the second surface 128. The RDL 123 may comprise one or more transmission lines 127. The electronics system 121 is electrically connected to the electric contacts 125 and the transmission lines 127 through the vias 126. The RDL 123 is particularly useful when multiple chips each with an electronic layer 120 are arranged in an array to form a detector with a larger size, or when the electronic layer 120 is bigger than an area that can be exposed simultaneously in a photolithography process.

The substrate 122 may be a thinned substrate. For example, the substrate may have a thickness of 750 microns or less, 200 microns or less, 100 microns or less, 50 microns or less, 20 microns or less, or 5 microns or less. The substrate 122 may be a silicon substrate or a substrate or other suitable semiconductor or insulator. The substrate 122 may be produced by grinding a thicker substrate to a desired thickness.

The one or more electric contacts 125 may be a layer of metal or doped semiconductor. For example, the electric contacts 125 may be gold, copper, platinum, palladium, doped silicon, etc.

The vias 126 pass through the substrate 122 and electrically connect electrical components (e.g., the electrical contacts 125) on the first surface 124 to electrical components (e.g., the RDL) on the second surface 128. The vias 126 may be used to provide electrical power and transmit signals to and from the electrical components in the detector 100. The vias 126 are sometimes referred to as "through-silicon vias" although they may be fabricated in substrates of materials other than silicon.

The RDL 123 may comprise one or more transmission lines 127. The transmission lines 127 electrically connect electrical components (e.g., the vias 126) in the substrate 122 to bonding pads at other locations on the substrate 122. The transmission lines 127 may be electrically isolated from the substrate 122 except at certain vias 126 and certain bonding pads. The transmission lines 127 may be a material with small attenuation of X-ray, such as Al. The RDL 123 may redistribute electrical connections to more convenient locations.

Figure 3B:
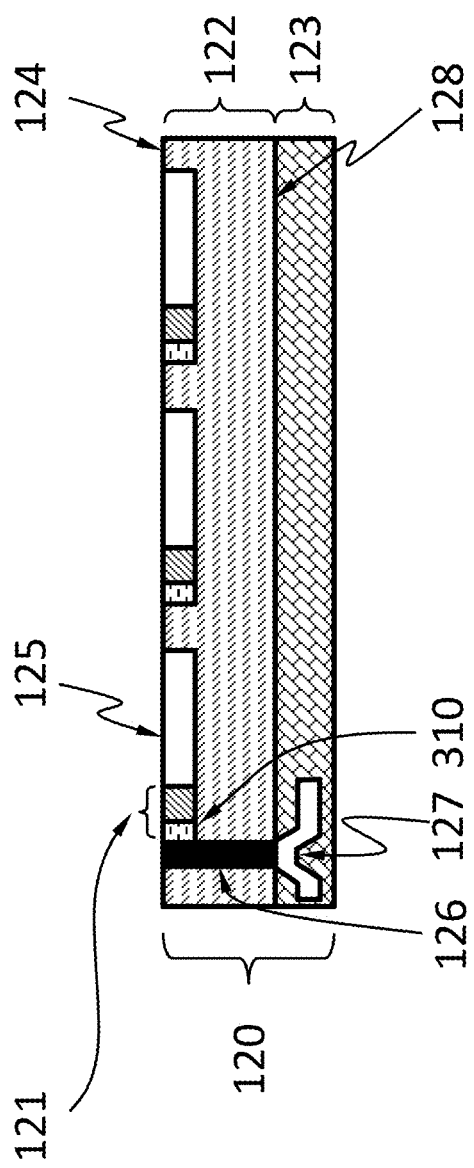
FIG. 3B schematically shows the electronics layer 120 according to an embodiment.

FIG. 3B schematically shows the electronics layer 120 according to an embodiment similar to the embodiment shown in FIG. 3A. Each of the electrical contacts 125 may have its dedicated controller 310.

Figure 3C:
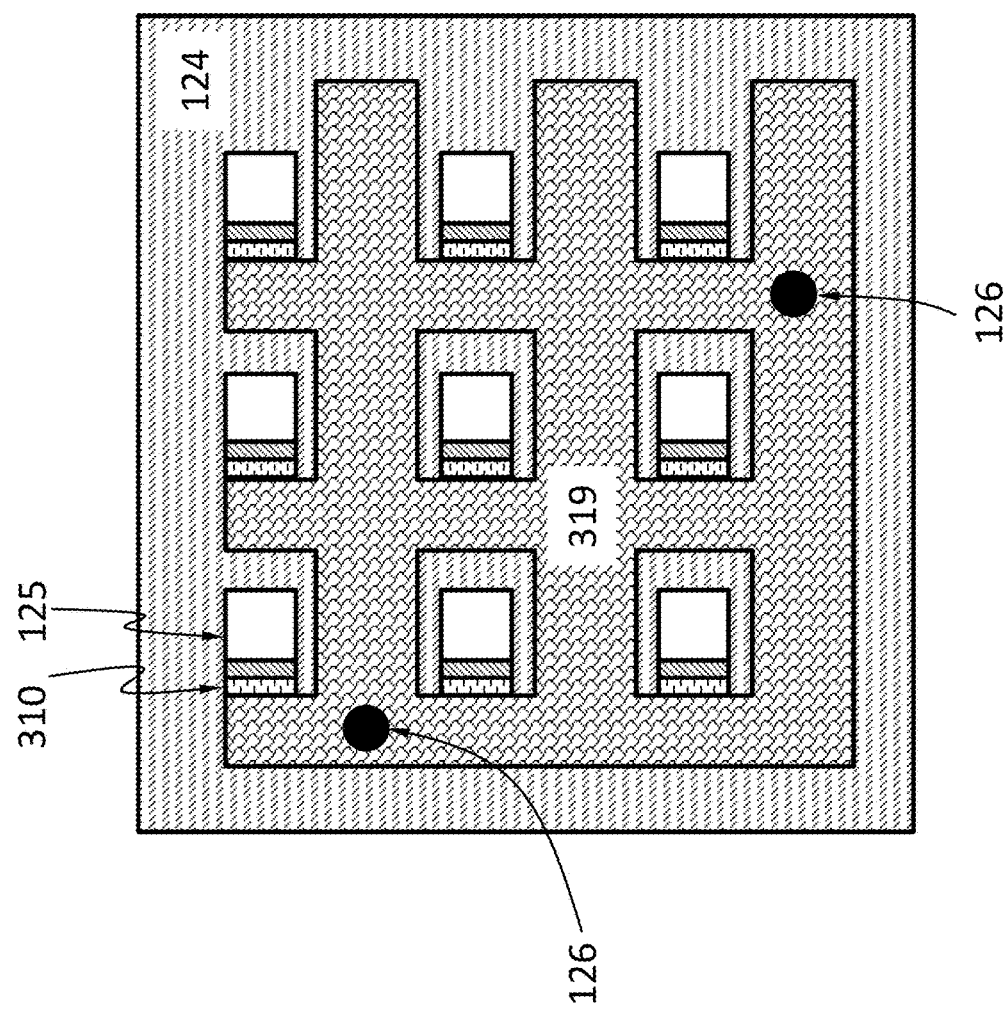
FIG. 3C schematically shows a top view of the electronics layer 120 according to an embodiment.
Figure 3D:
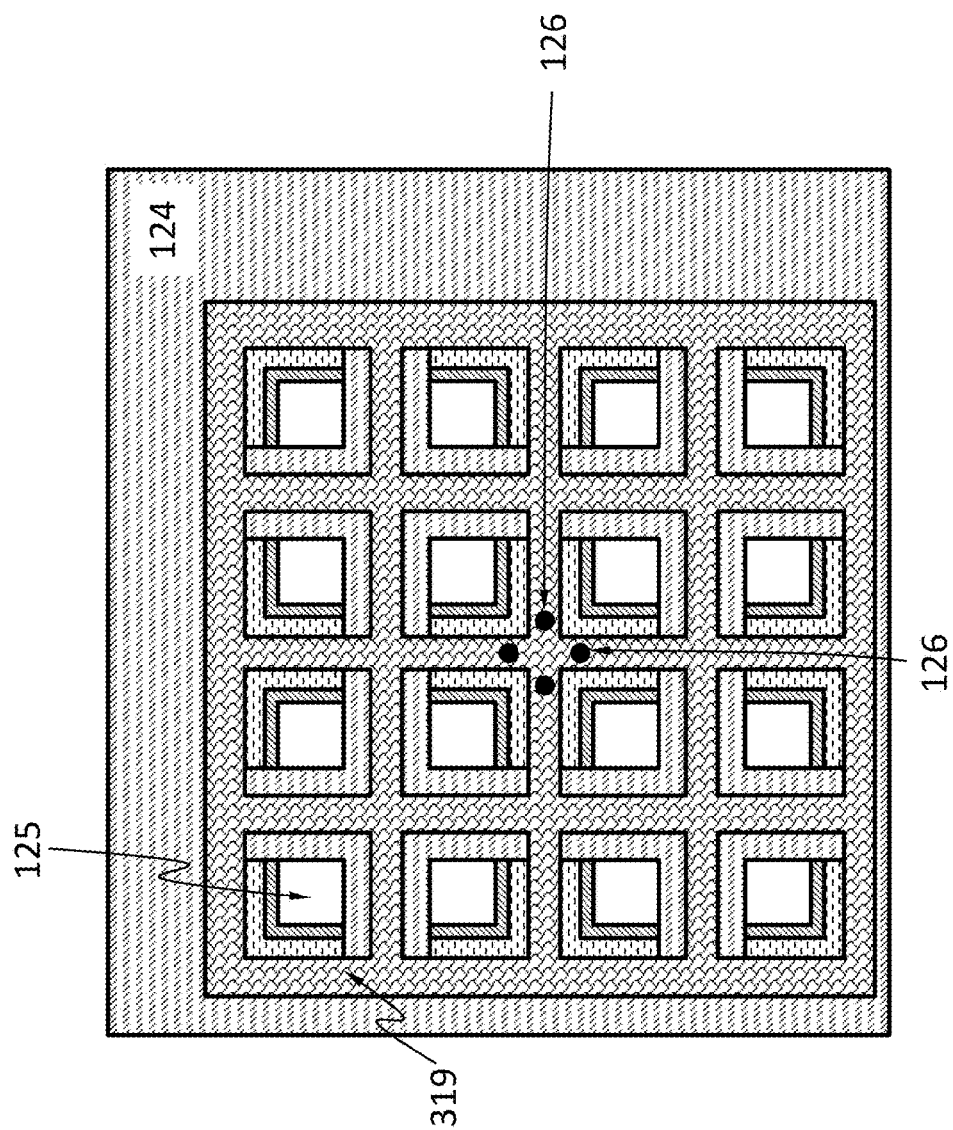
FIG. 3D schematically shows a top view of the electronics layer 120 according to an embodiment.

FIG. 3C schematically shows a top view of the electronics layer 120 according to an embodiment where a group of electrical contacts 125 share a peripheral circuit 319. The peripheral circuit 319 may be arranged on the first surface 124 in areas not occupied by other components (e.g., the group of electrical contacts 125, and the electronic system 121. If the electronics layer 120 is fabricated using photolithography, all or some of the electrical contacts 125 within an area exposed simultaneously may share one peripheral circuit 319. The peripheral circuit 319 may be connected to more than one transmission line 127 by more than one vias 126. FIG. 3D schematically shows a top view of the electronics layer 120 according to an embodiment, with a different arrangement of the peripheral circuit 319. The arrangement of the peripheral circuit 319 is not limited to these examples. The peripheral circuit 319 may have redundancy. Redundancy allows the semiconductor X-ray detector 100 not to be disabled due to a partial failure of the peripheral circuit 319. If one part of the peripheral circuit 319 fails, another part may be activated. For example, if multiple pixels share the same peripheral circuit 319, total failure of the peripheral circuit 319 will disable all these pixels and likely render the entire detector 100 inoperable. Having redundancy reduces the chance of total failure. The peripheral circuit 319 may be configured to perform various functions, such as multiplexing, input/output, providing power, data caching, etc.

Figure 3E:
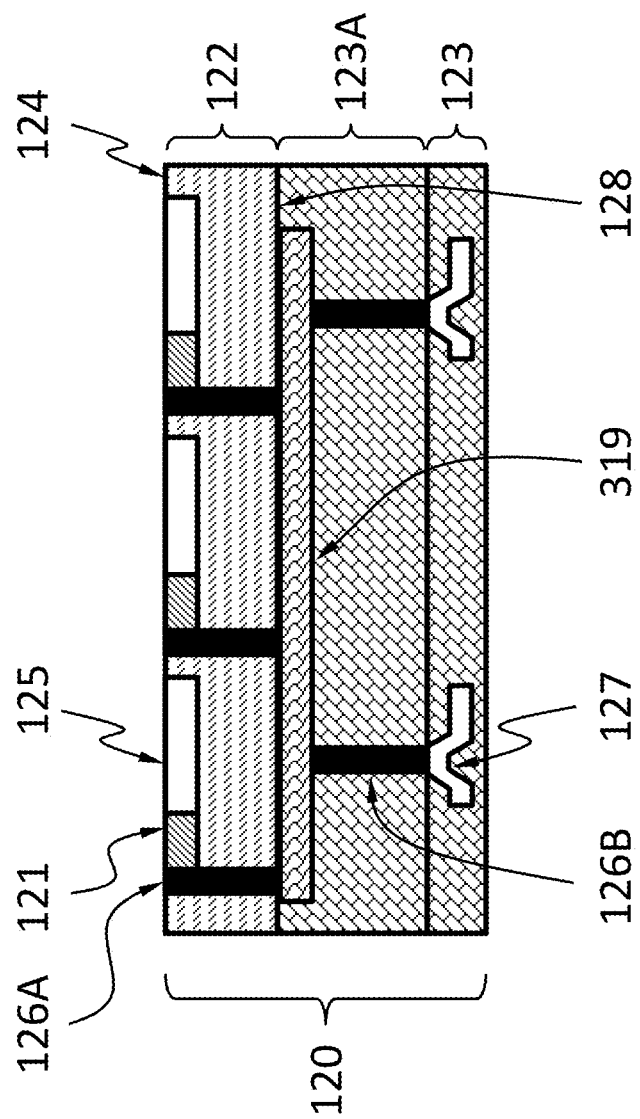
FIG. 3E schematically shows a cross-sectional view of the electronics layer 120 according to an embodiment.

The peripheral circuit 319 is not necessarily arranged on the first surface. FIG. 3E schematically shows a cross-sectional view of the electronics layer 120 according to an embodiment where the peripheral circuit 319 is arranged on a surface 128 of a substrate 123A sandwiched between the substrate 122 and the RDL 123. The peripheral circuit 319 may be electrically connected to the electrical contacts 125 by a first group of vias 126A extending in the substrate 122 and electrically connected to the transmission lines 127 by a second group of vias 126B extending in the substrate 123A. Each of the electrical contacts 125 may have a dedicated vias 126A for connection to the peripheral circuit 319. The peripheral circuit 319 may be arranged on multiple surfaces.

FIG. 4A schematically shows direct bonding between the X-ray absorption layer 110 and the electronic layer 120 at discrete portion of the electrical contact 119B and the electrical contacts 125. Direct bonding is a wafer bonding process without any additional intermediate layers (e.g., solder bumps). The bonding process is based on chemical bonds between two surfaces. Direct bonding may be at elevated temperature but not necessarily so.

Figure 4B:
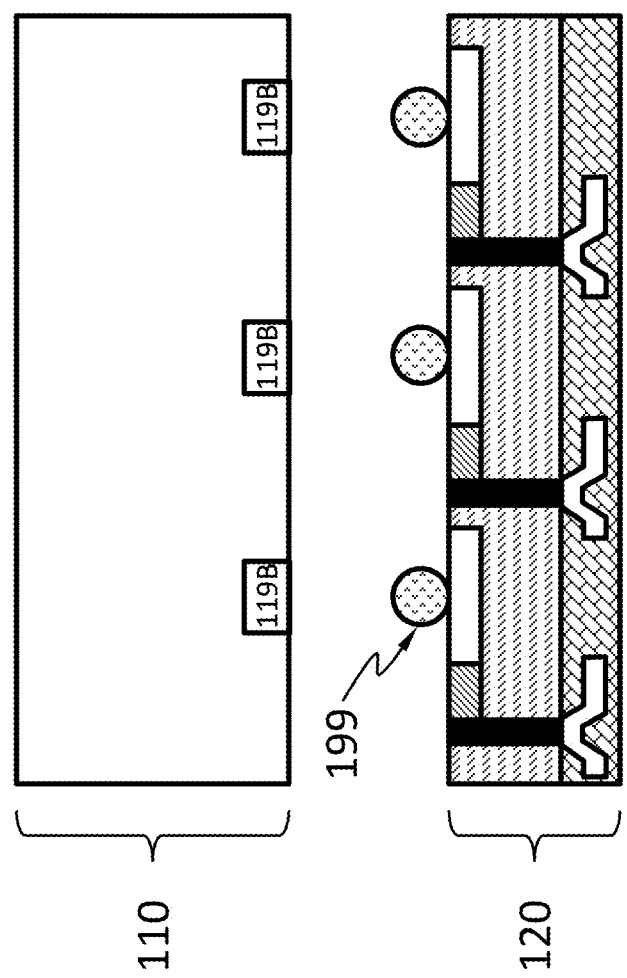
FIG. 4B schematically shows flip chip bonding between an X-ray absorption layer and an electronic layer.

FIG. 4B schematically shows flip chip bonding between the X-ray absorption layer 110 and the electronic layer 120 at discrete portion of the electrical contact 119B and the electrical contacts 125. Flip chip bonding uses solder bumps 199 deposited onto contact pads (e.g., the electrodes of the X-ray absorption layer 110 or the electrical contacts 125). Either the X-ray absorption layer 110 or the electronic layer 120 is flipped over and the electrodes of the X-ray absorption layer 110 are aligned to the electrical contacts 125. The solder bumps 199 may be melted to solder the electrodes and the electrical contacts 125 together. Any void space among the solder bumps 199 may be filled with an insulating material. Other materials such as thermal copper or gold pillar bump may be used to achieve similar function as solder bumps.

Figure 5:
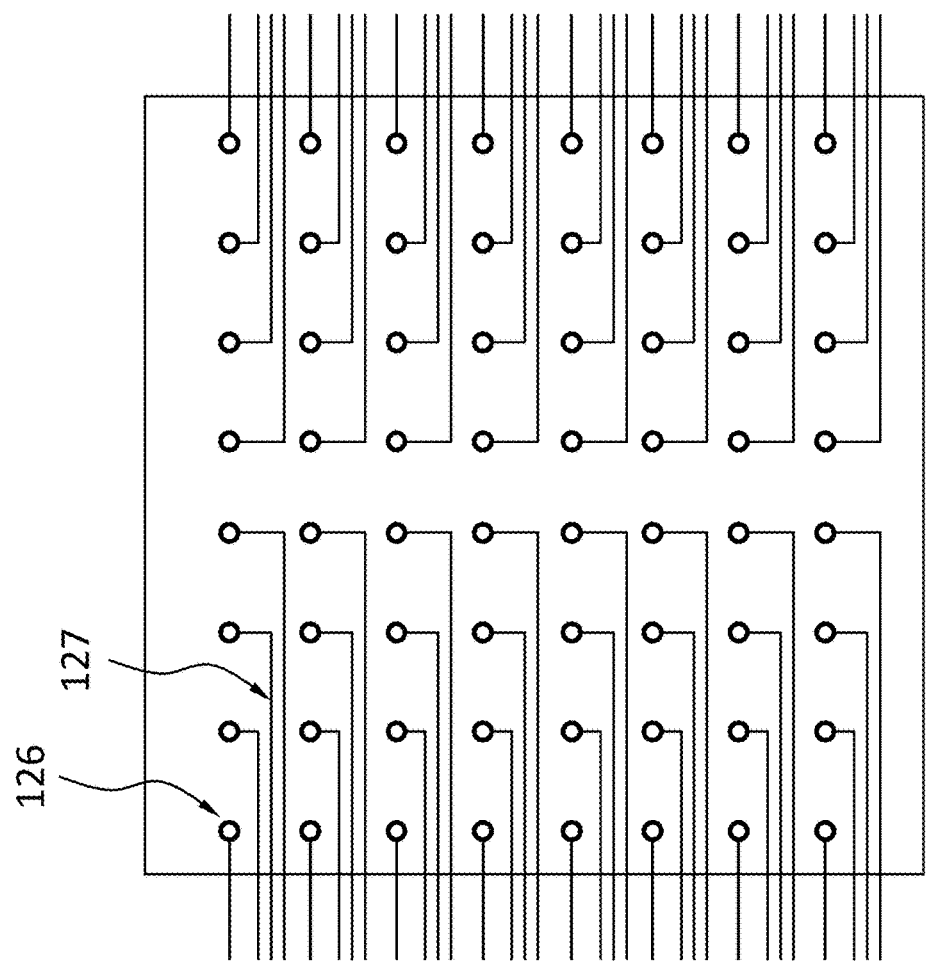
FIG. 5 schematically shows a bottom view of the electronic layer.

FIG. 5 schematically shows a bottom view of the RDL 123, with other components obstructing the view omitted. The transmission lines 127 can be seen to electrically connect to vias 126 and redistribute vias 126 to other locations.

Figure 6A:
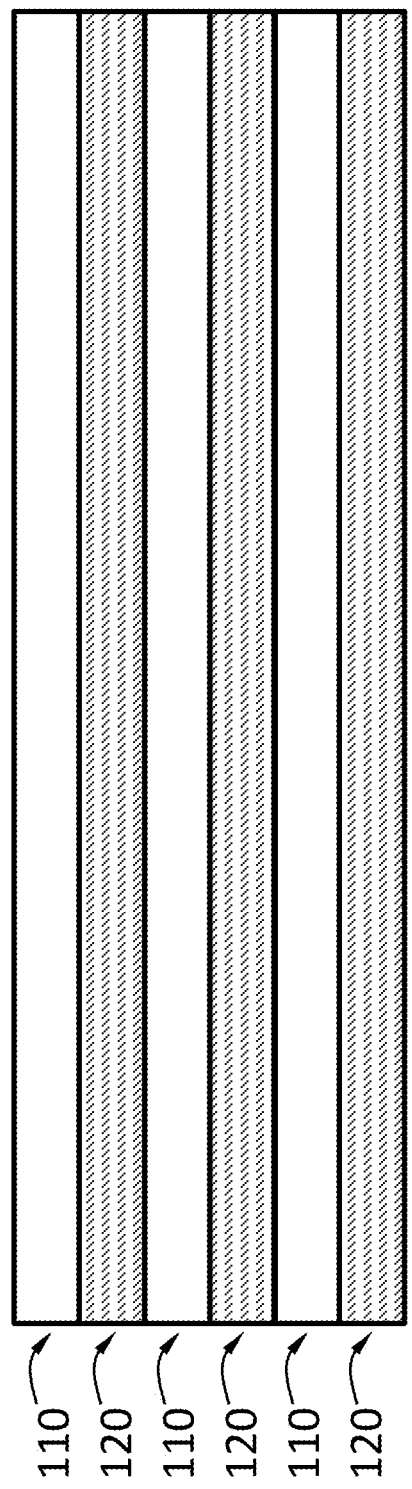
FIG. 6A shows that the electronics layer as shown in FIG. 3A, FIG. 3B, FIG. 3C, FIG. 3D, or FIG. 3E allows stacking multiple semiconductor X-ray detectors.

FIG. 6A shows that the electronics layer 120 as shown in FIG. 3A, FIG. 3B, FIG. 3C, FIG. 3D, or FIG. 3E allows stacking multiple semiconductor X-ray detectors 100 because the RDL 123 and the vias 126 facilitate routing of signal paths through multiple layers and because the electronic system 121 as described below may have low enough power consumption to eliminate bulky cooling mechanisms. The multiple semiconductor X-ray detectors 100 in the stack do not have to be identical. For example, the multiple semiconductor X-ray detectors 100 may differ in thickness, structure, or material.

Figure 6B:
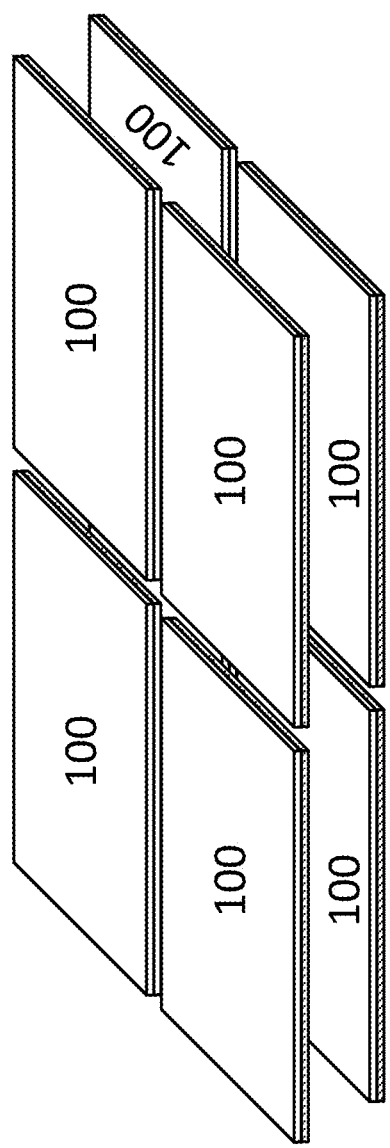
FIG. 6B schematically shows a top view of multiple semiconductor X-ray detectors 100 stacked.

FIG. 6B schematically shows a top view of multiple semiconductor X-ray detectors 100 stacked. Each layer may have multiple detectors 100 tiled to cover a larger area. The tiled detectors 100 in one layer can be staggered relative to the tiled detectors 100 in another layer, which may eliminate gaps in which incident X-ray photons cannot be detected.

According to an embodiment, the semiconductor X-ray detector 100 may be fabricated using a method including: obtaining an X-ray absorption layer comprising an electrode; obtaining an electronics layer, the electronics layer comprising: a substrate having a first surface and a second surface, an electronics system in or on the substrate, an electric contact on the first surface, a via, and a redistribution layer (RDL) on the second surface; bonding the X-ray absorption layer and the electronics layer such that the electrode is electrically connected to the electric contact; wherein the RDL comprises a transmission line; wherein the via extends from the first surface to the second surface; wherein the electronics system is electrically connected to the electric contact and the transmission line through the via.

Figure 7A:
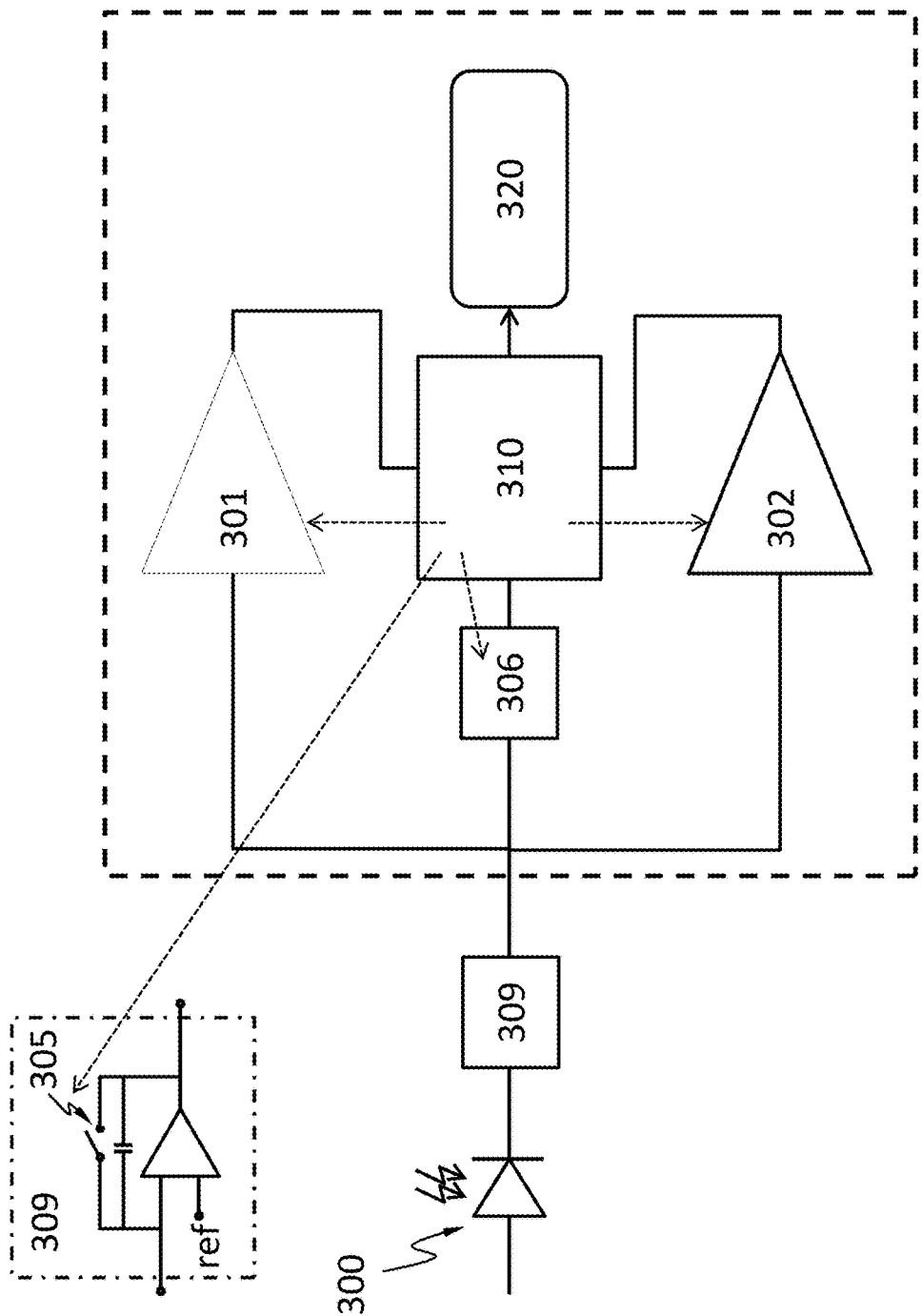
FIG. 7A and FIG. 7B each show a component diagram of an electronic system of the detector in FIG. 1A or FIG. 1B, according to an embodiment.
Figure 7B:
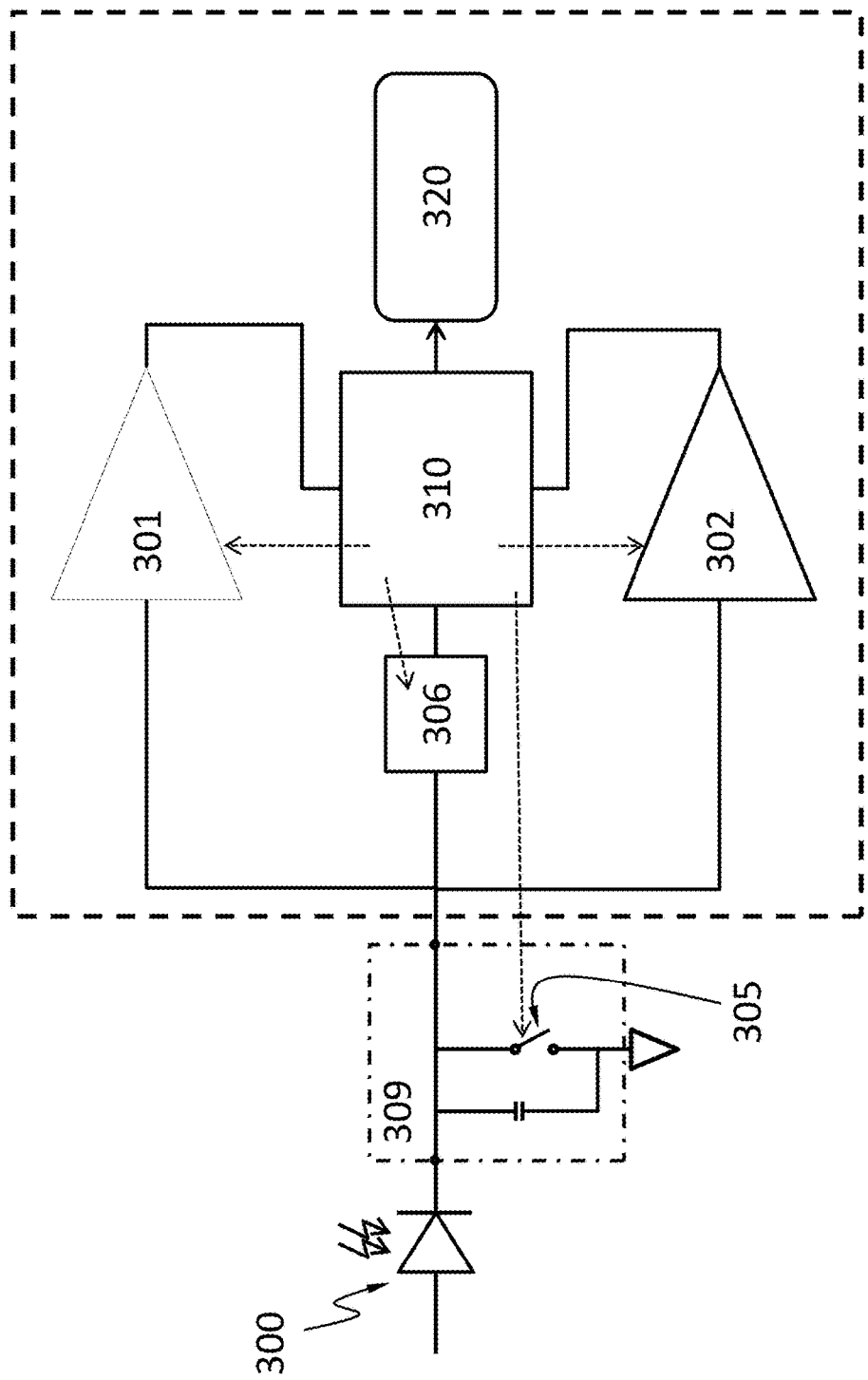

FIG. 7A and FIG. 7B each show a component diagram of the electronic system 121, according to an embodiment. The electronic system 121 may include a first voltage comparator 301, a second voltage comparator 302, a counter 320, a switch 305, a voltmeter 306 and a controller 310.

The first voltage comparator 301 is configured to compare the voltage of an electrode of a diode 300 to a first threshold. The diode may be a diode formed by the first doped region 111, one of the discrete regions 114 of the second doped region 113, and the optional intrinsic region 112. Alternatively, the first voltage comparator 301 is configured to compare the voltage of an electrical contact (e.g., a discrete portion of electrical contact 119B) to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 5-10%, 10%-20%, 20-30%, 30-40% or 40-50% of the maximum voltage one incident X-ray photon may generate in the diode or the resistor. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. The second threshold may be at least 50% of the maximum voltage one incident X-ray photon may generate in the diode or resistor. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counter 320 is configured to register a number of X-ray photons reaching the diode or resistor. The counter 320 may be a software component (e.g., a number stored in a computer memory) or a hardware component (e.g., a 4017 IC and a 7490 IC).

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire before or after the voltage becomes stable, i.e., the rate of change of the voltage is substantially zero. The phase "the rate of change of the voltage is substantially zero" means that temporal change of the voltage is less than 0.1%/ns. The phase "the rate of change of the voltage is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by the counter 320 to increase by one, if, during the time delay, the second voltage comparator 302 determines that the absolute value of the voltage equals or exceeds the absolute value of the second threshold.

The controller 310 may be configured to cause the voltmeter 306 to measure the voltage upon expiration of the time delay. The controller 310 may be configured to connect the electrode to an electrical ground, so as to reset the voltage and discharge any charge carriers accumulated on the electrode. In an embodiment, the electrode is connected to an electrical ground after the expiration of the time delay. In an embodiment, the electrode is connected to an electrical ground for a finite reset time period. The controller 310 may connect the electrode to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The voltmeter 306 may feed the voltage it measures to the controller 310 as an analog or digital signal.

Figure 8:
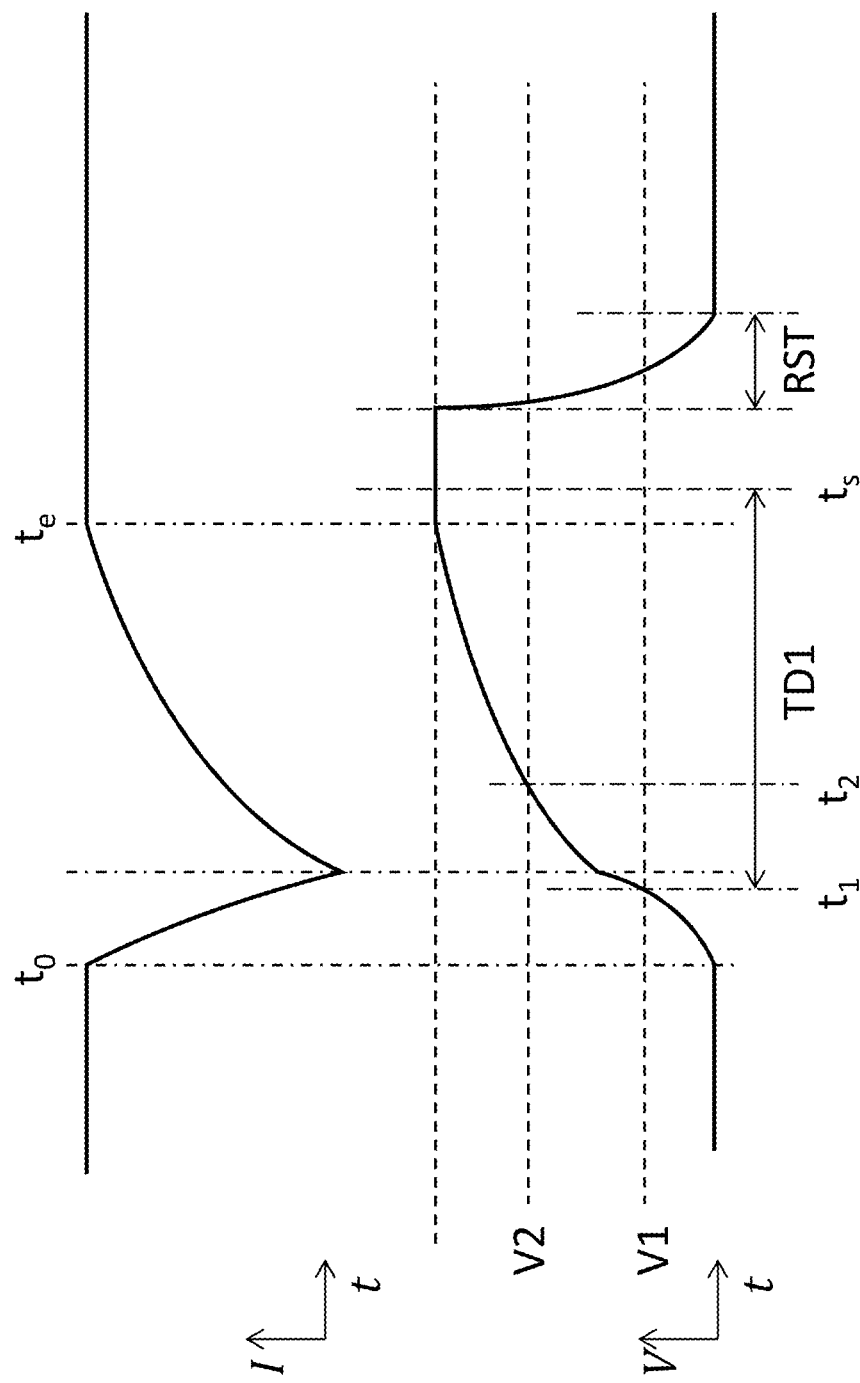
FIG. 8 schematically shows a temporal change of the electric current flowing through an electrode (upper curve) of a diode or an electrical contact of a resistor of an X-ray absorption layer exposed to X-ray, the electric current caused by charge carriers generated by an X-ray photon incident on the X-ray absorption layer, and a corresponding temporal change of the voltage of the electrode (lower curve), according to an embodiment.

The system 121 may include a capacitor module 309 electrically connected to the electrode of the diode 300 or which electrical contact, wherein the capacitor module is configured to collect charge carriers from the electrode. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 8, between to $t_0$ $t_1$, or $t_1$-$t_2$). After the integration period has expired, the capacitor voltage is sampled and then reset by a reset switch. The capacitor module can include a capacitor directly connected to the electrode.

FIG. 8 schematically shows a temporal change of the electric current flowing through the electrode (upper curve) caused by charge carriers generated by an X-ray photon incident on the diode or the resistor, and a corresponding temporal change of the voltage of the electrode (lower curve). The voltage may be an integral of the electric current with respect to time. At time $t_0$, the X-ray photon hits the diode or the resistor, charge carriers start being generated in the diode or the resistor, electric current starts to flow through the electrode of the diode or the resistor, and the absolute value of the voltage of the electrode or electrical contact starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_s$, the time delay TD1 expires. In the example of FIG. 8, time $t_s$ is after time $t_e$; namely TD1 expires after all charge carriers generated by the X-ray photon drift out of the X-ray absorption layer 110. The rate of change of the voltage is thus substantially zero at $t_s$. The controller 310 may be configured to deactivate the second voltage comparator 302 at expiration of TD1 or at $t_2$, or any time in between.

The controller 310 may be configured to cause the voltmeter 306 to measure the voltage upon expiration of the time delay TD1. In an embodiment, the controller 310 causes the voltmeter 306 to measure the voltage after the rate of change of the voltage becomes substantially zero after the expiration of the time delay TD1. The voltage at this moment is proportional to the amount of charge carriers generated by an X-ray photon, which relates to the energy of the X-ray photon. The controller 310 may be configured to determine the energy of the X-ray photon based on voltage the voltmeter 306 measures. One way to determine the energy is by binning the voltage. The counter 320 may have a sub-counter for each bin. When the controller 310 determines that the energy of the X-ray photon falls in a bin, the controller 310 may cause the number registered in the sub-counter for that bin to increase by one. Therefore, the system 121 may be able to detect an X-ray image and may be able to resolve X-ray photon energies of each X-ray photon.

After TD1 expires, the controller 310 connects the electrode to an electric ground for a reset period RST to allow charge carriers accumulated on the electrode to flow to the ground and reset the voltage. After RST, the system 121 is ready to detect another incident X-ray photon. Implicitly, the rate of incident X-ray photons the system 121 can handle in the example of FIG. 8 is limited by 1/(TD1+RST). If the first voltage comparator 301 has been deactivated, the controller 310 can activate it at any time before RST expires. If the controller 310 has been deactivated, it may be activated before RST expires.

Figure 9:
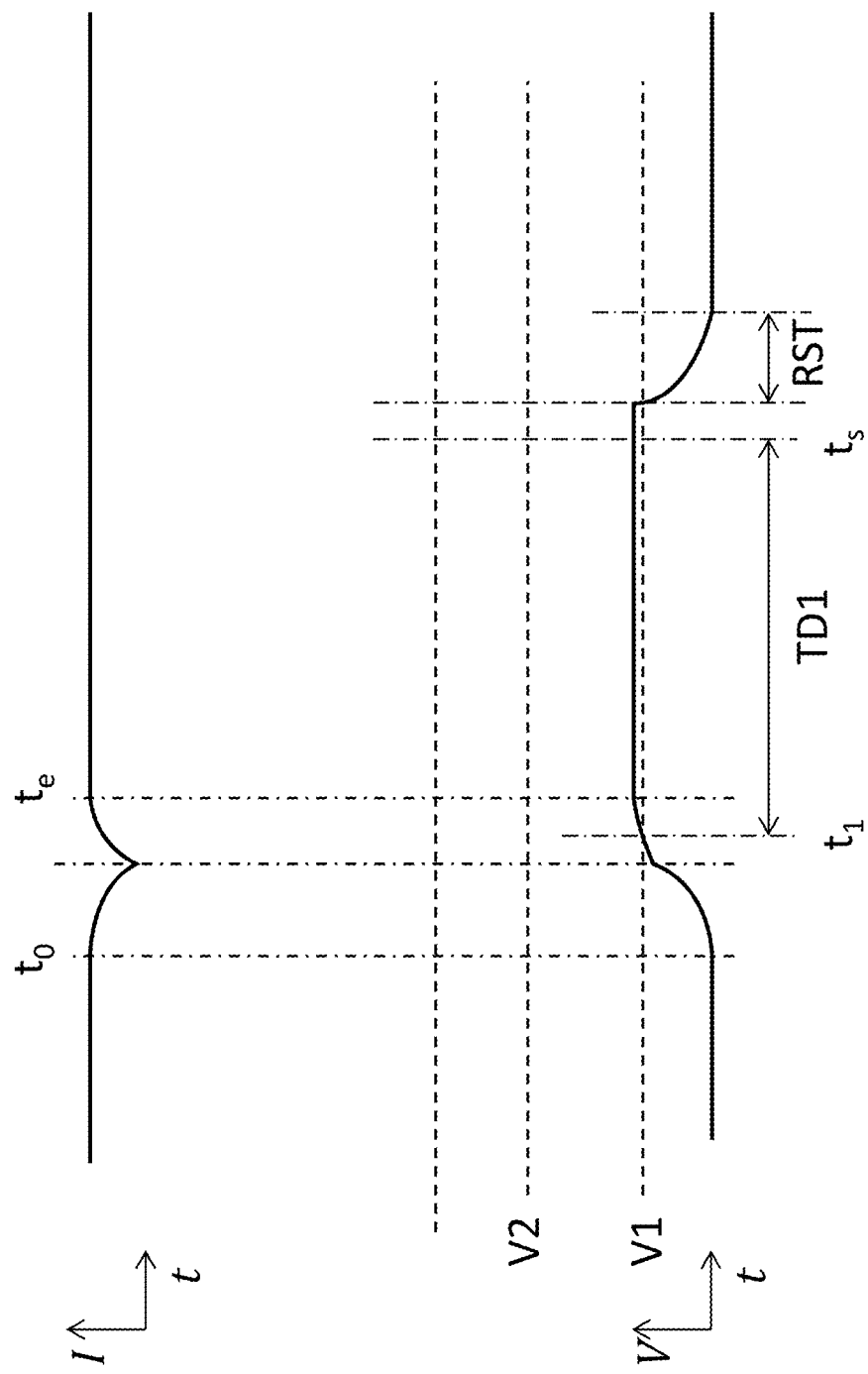
FIG. 9 schematically shows a temporal change of the electric current flowing through the electrode (upper curve) caused by noise (e.g., dark current), and a corresponding temporal change of the voltage of the electrode (lower curve), in the electronic system operating in the way shown in FIG. 8, according to an embodiment.

FIG. 9 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 8. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD1 and the controller 310 may deactivate the first voltage comparator 301 at the beginning of TD1. During TD1 (e.g., at expiration of TD1), the controller 310 activates the second voltage comparator 302. The noise is very unlikely large enough to cause the absolute value of the voltage to exceed the absolute value of V2 during TD1. Therefore, the controller 310 does not cause the number registered by the counter 320 to increase. At time $t_e$, the noise ends. At time $t_s$, the time delay TD1 expires. The controller 310 may be configured to deactivate the second voltage comparator 302 at expiration of TD1. The controller 310 may be configured not to cause the voltmeter 306 to measure the voltage if the absolute value of the voltage does not exceed the absolute value of V2 during TD1. After TD1 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 10:
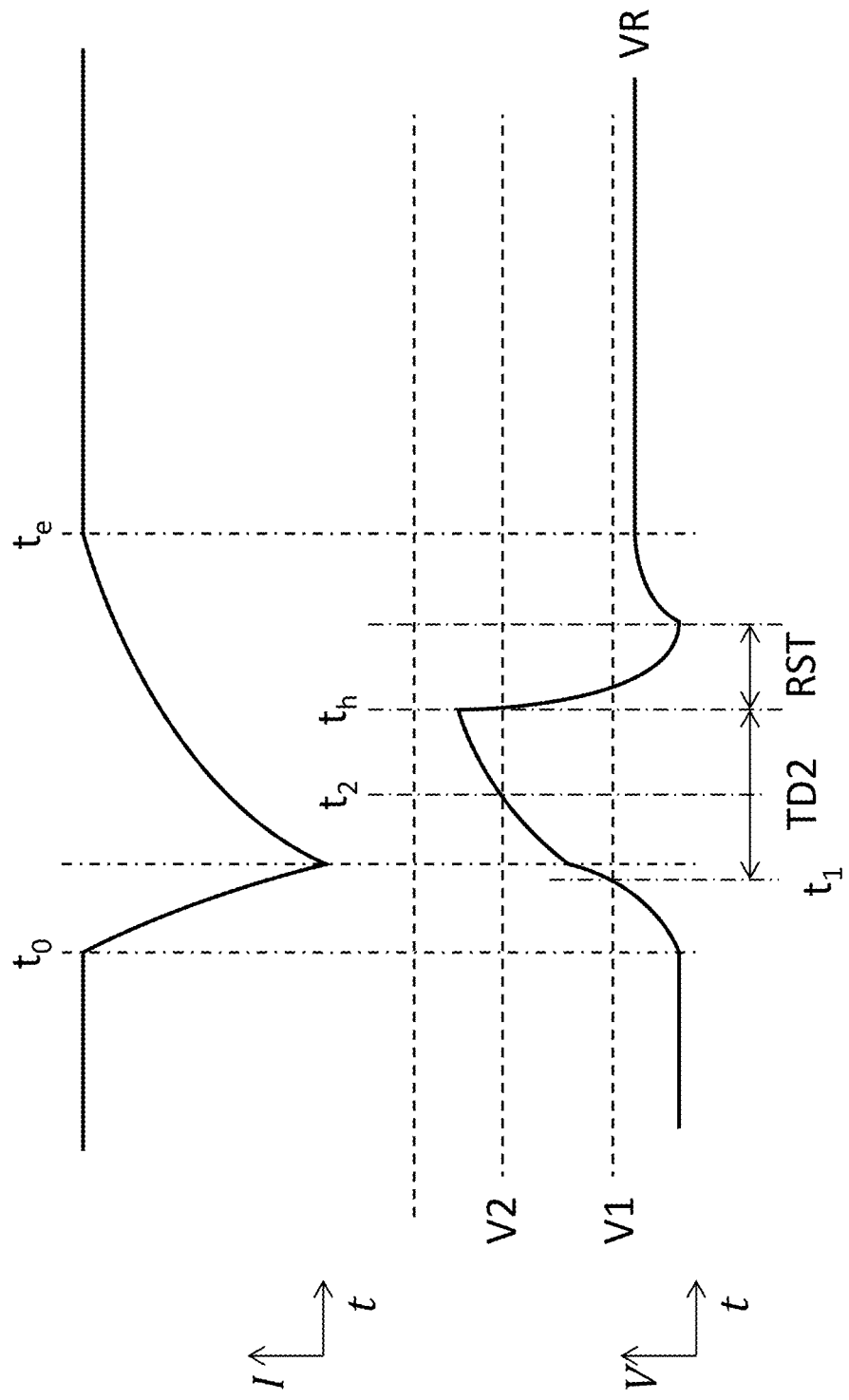
FIG. 10 schematically shows a temporal change of the electric current flowing through an electrode (upper curve) of the X-ray absorption layer exposed to X-ray, the electric current caused by charge carriers generated by an X-ray photon incident on the X-ray absorption layer, and a corresponding temporal change of the voltage of the electrode (lower curve), when the electronic system operates to detect incident X-ray photons at a higher rate, according to an embodiment.

FIG. 10 schematically shows a temporal change of the electric current flowing through the electrode (upper curve) caused by charge carriers generated by an X-ray photon incident on the diode or the resistor, and a corresponding temporal change of the voltage of the electrode (lower curve), when the system 121 operates to detect incident X-ray photons at a rate higher than 1/(TD1+RST). The voltage may be an integral of the electric current with respect to time. At time $t_0$, the X-ray photon hits the diode or the resistor, charge carriers start being generated in the diode or the resistor, electric current starts to flow through the electrode of the diode or the electrical contact of resistor, and the absolute value of the voltage of the electrode or the electrical contact starts to increase. At time $t_1$, the first voltage comparator 301 determines that the absolute value of the voltage equals or exceeds the absolute value of the first threshold V1, and the controller 310 starts a time delay TD2 shorter than TD1, and the controller 310 may deactivate the first voltage comparator 301 at the beginning of TD2. If the controller 310 is deactivated before $t_1$, the controller 310 is activated at $t_1$. During TD2 (e.g., at expiration of TD2), the controller 310 activates the second voltage comparator 302. If during TD2, the second voltage comparator 302 determines that the absolute value of the voltage equals or exceeds the absolute value of the second threshold at time $t_2$, the controller 310 causes the number registered by the counter 320 to increase by one. At time $t_e$, all charge carriers generated by the X-ray photon drift out of the X-ray absorption layer 110. At time $t_h$, the time delay TD2 expires. In the example of FIG. 10, time $t_h$ is before time $t_e$; namely TD2 expires before all charge carriers generated by the X-ray photon drift out of the X-ray absorption layer 110. The rate of change of the voltage is thus substantially non-zero at $t_h$. The controller 310 may be configured to deactivate the second voltage comparator 302 at expiration of TD2 or at $t_2$, or any time in between.

The controller 310 may be configured to extrapolate the voltage at $t_e$ from the voltage as a function of time during TD2 and use the extrapolated voltage to determine the energy of the X-ray photon.

After TD2 expires, the controller 310 connects the electrode to an electric ground for a reset period RST to allow charge carriers accumulated on the electrode to flow to the ground and reset the voltage. In an embodiment, RST expires before $t_e$. The rate of change of the voltage after RST may be substantially non-zero because all charge carriers generated by the X-ray photon have not drifted out of the X-ray absorption layer 110 upon expiration of RST before $t_e$. The rate of change of the voltage becomes substantially zero after $t_e$ and the voltage stabilized to a residue voltage VR after $t_e$. In an embodiment, RST expires at or after $t_e$, and the rate of change of the voltage after RST may be substantially zero because all charge carriers generated by the X-ray photon drift out of the X-ray absorption layer 110 at $t_e$. After RST, the system 121 is ready to detect another incident X-ray photon. If the first voltage comparator 301 has been deactivated, the controller 310 can activate it at any time before RST expires. If the controller 310 has been deactivated, it may be activated before RST expires.

Figure 11:
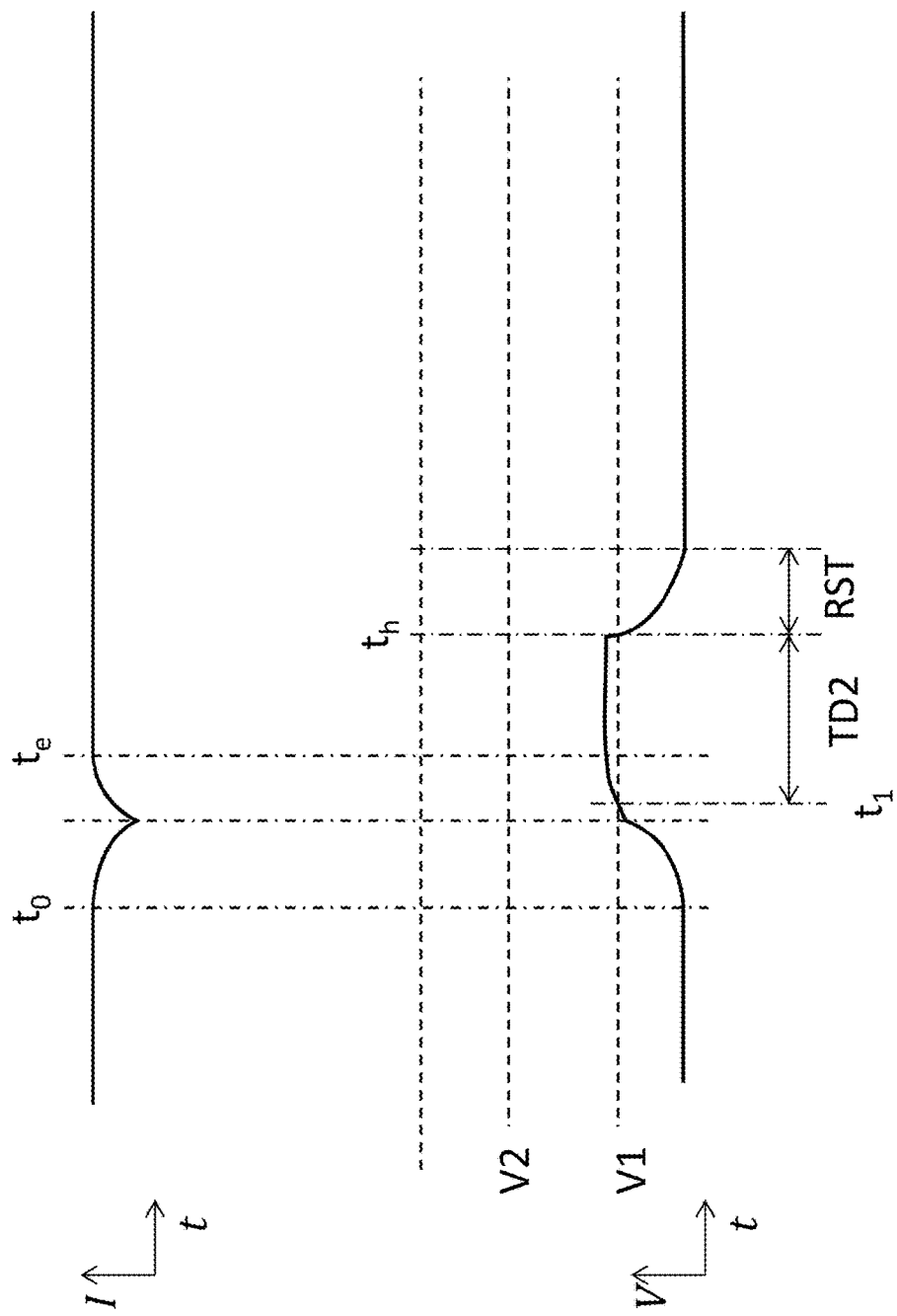
FIG. 11 schematically shows a temporal change of the electric current flowing through the electrode (upper curve) caused by noise (e.g., dark current), and a corresponding temporal change of the voltage of the electrode (lower curve), in the electronic system operating in the way shown in FIG. 10, according to an embodiment.

FIG. 11 schematically shows a temporal change of the electric current flowing through the electrode (upper curve) caused by noise (e.g., dark current, background radiation, scattered X-rays, fluorescent X-rays, shared charges from adjacent pixels), and a corresponding temporal change of the voltage of the electrode (lower curve), in the system 121 operating in the way shown in FIG. 10. At time $t_0$, the noise begins. If the noise is not large enough to cause the absolute value of the voltage to exceed the absolute value of V1, the controller 310 does not activate the second voltage comparator 302. If the noise is large enough to cause the absolute value of the voltage to exceed the absolute value of V1 at time $t_1$ as determined by the first voltage comparator 301, the controller 310 starts the time delay TD2 and the controller 310 may deactivate the first voltage comparator 301 at the beginning of TD2. During TD2 (e.g., at expiration of TD2), the controller 310 activates the second voltage comparator 302. The noise is very unlikely large enough to cause the absolute value of the voltage to exceed the absolute value of V2 during TD2. Therefore, the controller 310 does not cause the number registered by the counter 320 to increase. At time $t_e$, the noise ends. At time $t_h$, the time delay TD2 expires. The controller 310 may be configured to deactivate the second voltage comparator 302 at expiration of TD2. After TD2 expires, the controller 310 connects the electrode to an electric ground for a reset period RST to allow charge carriers accumulated on the electrode as a result of the noise to flow to the ground and reset the voltage. Therefore, the system 121 may be very effective in noise rejection.

Figure 12:
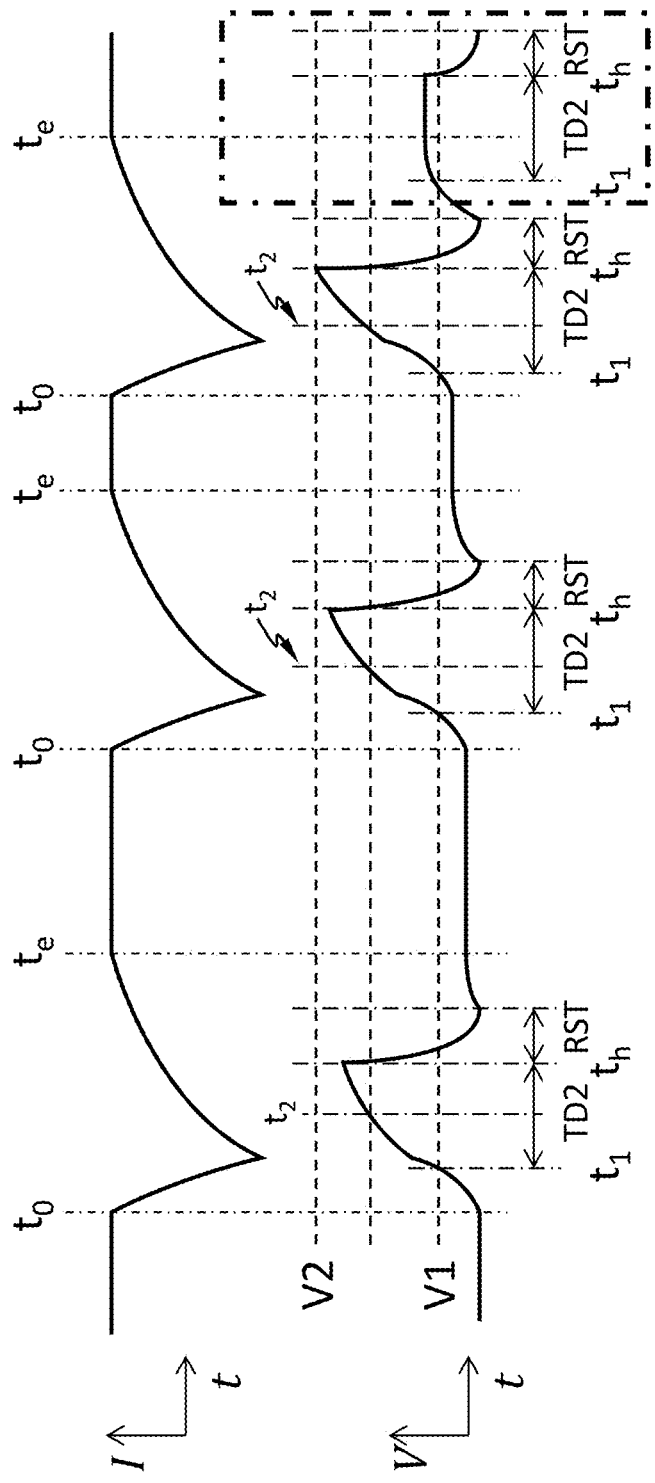
FIG. 12 schematically shows a temporal change of the electric current flowing through the electrode (upper curve) caused by charge carriers generated by a series of X-ray photons incident on the X-ray absorption layer, and a corresponding temporal change of the voltage of the electrode, in the electronic system operating in the way shown in FIG. 10 with RST expires before $t_e$, according to an embodiment.

FIG. 12 schematically shows a temporal change of the electric current flowing through the electrode (upper curve) caused by charge carriers generated by a series of X-ray photons incident on the diode or the resistor, and a corresponding temporal change of the voltage of the electrode (lower curve), in the system 121 operating in the way shown in FIG. 10 with RST expires before $t_e$. The voltage curve caused by charge carriers generated by each incident X-ray photon is offset by the residue voltage before that photon. The absolute value of the residue voltage successively increases with each incident photon. When the absolute value of the residue voltage exceeds V1 (see the dotted rectangle in FIG. 12), the controller starts the time delay TD2 and the controller 310 may deactivate the first voltage comparator 301 at the beginning of TD2. If no other X-ray photon incidence on the diode or the resistor during TD2, the controller connects the electrode to the electrical ground during the reset time period RST at the end of TD2, thereby resetting the residue voltage. The residue voltage thus does not cause an increase of the number registered by the counter 320.

Figure 13:
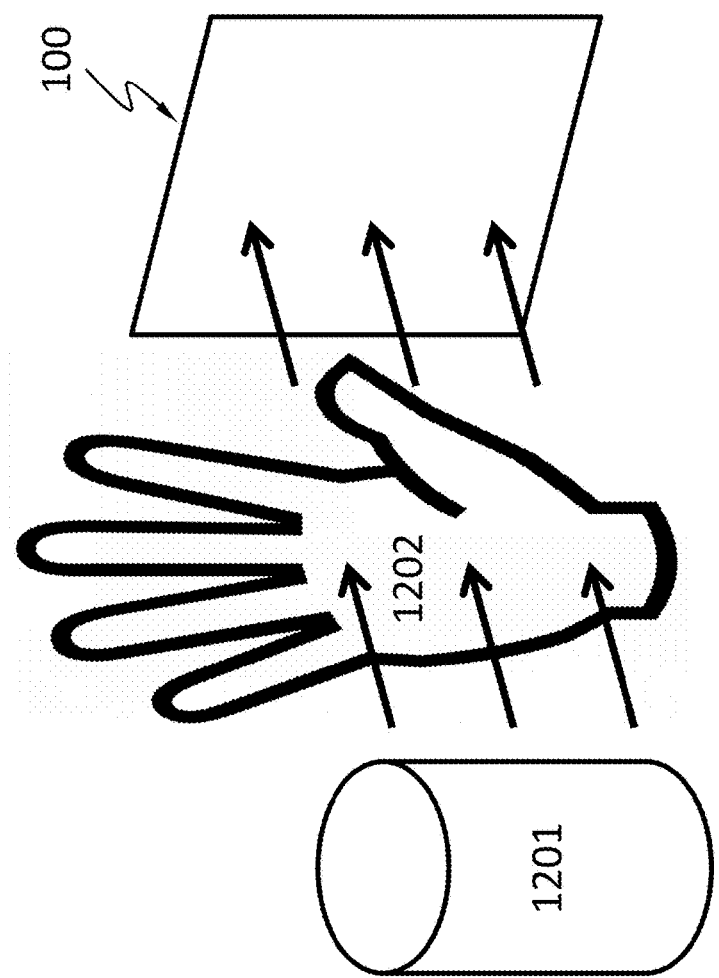
FIG. 13 schematically shows a system comprising the semiconductor X-ray detector described herein, suitable for medical imaging such as chest X-ray radiography, abdominal X-ray radiography, etc., according to an embodiment FIG. 14 schematically shows a system comprising the semiconductor X-ray detector described herein suitable for dental X-ray radiography, according to an embodiment.

FIG. 13 schematically shows a system comprising the semiconductor X-ray detector 100 described herein. The system may be used for medical imaging such as chest X-ray radiography, abdominal X-ray radiography, etc. The system comprises an X-ray source 1201. X-ray emitted from the X-ray source 1201 penetrates an object 1202 (e.g., a human body part such as chest, limb, abdomen), is attenuated by different degrees by the internal structures of the object 1202 (e.g., bones, muscle, fat and organs, etc.), and is projected to the semiconductor X-ray detector 100. The semiconductor X-ray detector 100 forms an image by detecting the intensity distribution of the X-ray.

Figure 14:
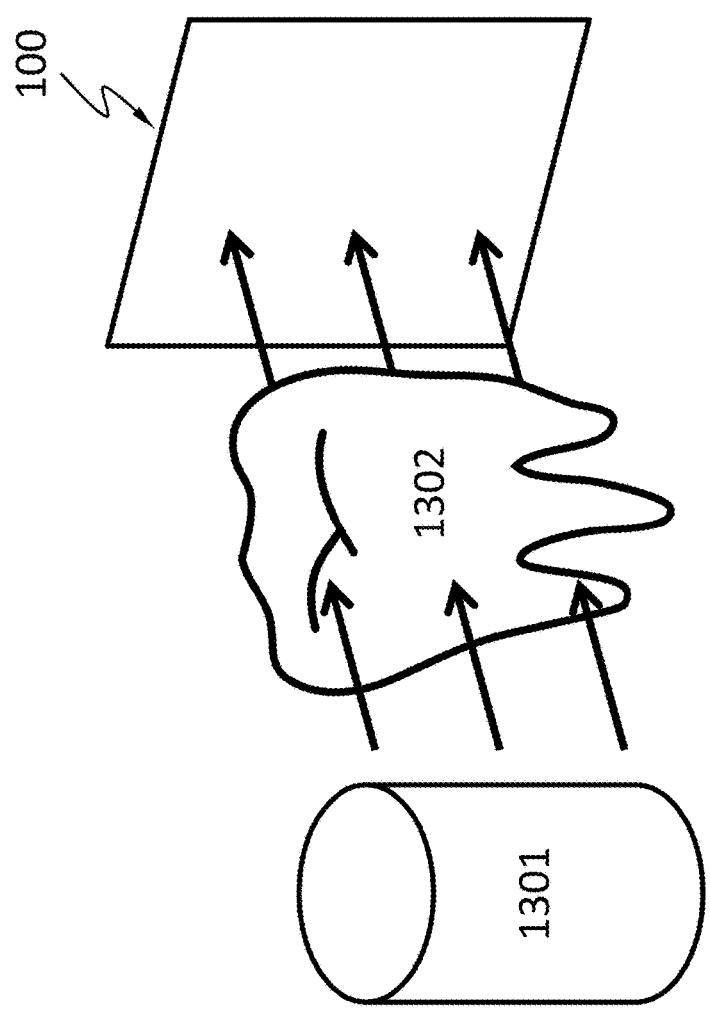

FIG. 14 schematically shows a system comprising the semiconductor X-ray detector 100 described herein. The system may be used for medical imaging such as dental X-ray radiography. The system comprises an X-ray source 1301. X-ray emitted from the X-ray source 1301 penetrates an object 1302 that is part of a mammal (e.g., human) mouth. The object 1302 may include a maxilla bone, a palate bone, a tooth, the mandible, or the tongue. The X-ray is attenuated by different degrees by the different structures of the object 1302 and is projected to the semiconductor X-ray detector 100. The semiconductor X-ray detector 100 forms an image by detecting the intensity distribution of the X-ray. Teeth absorb X-ray more than dental caries, infections, periodontal ligament. The dosage of X-ray radiation received by a dental patient is typically small (around 0.150 mSv for a full mouth series).

Figure 15:
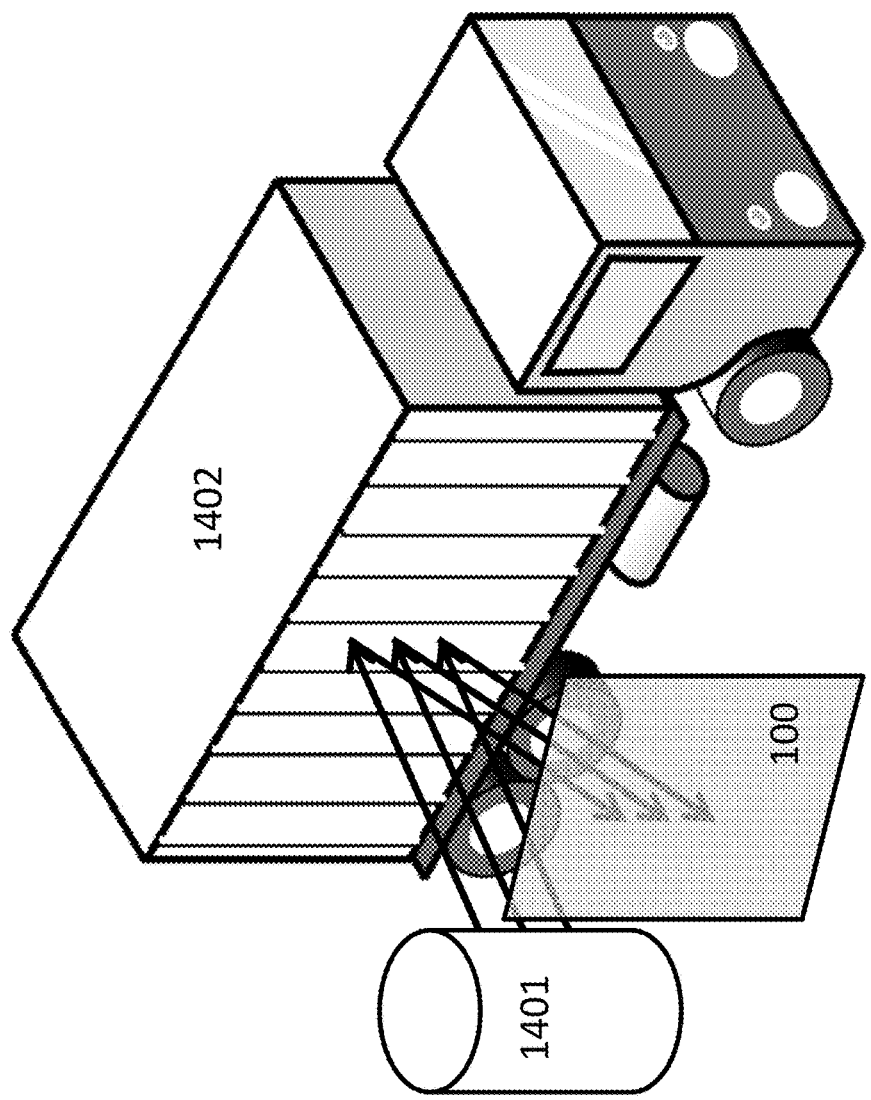
FIG. 15 schematically shows a cargo scanning or non-intrusive inspection (NII) system comprising the semiconductor X-ray detector described herein, according to an embodiment.

FIG. 15 schematically shows a cargo scanning or non-intrusive inspection (NII) system comprising the semiconductor X-ray detector 100 described herein. The system may be used for inspecting and identifying goods in transportation systems such as shipping containers, vehicles, ships, luggage, etc. The system comprises an X-ray source 1401. X-ray emitted from the X-ray source 1401 may backscatter from an object 1402 (e.g., shipping containers, vehicles, ships, etc.) and be projected to the semiconductor X-ray detector 100. Different internal structures of the object 1402 may backscatter X-ray differently. The semiconductor X-ray detector 100 forms an image by detecting the intensity distribution of the backscattered X-ray and/or energies of the backscattered X-ray photons.

Figure 16:
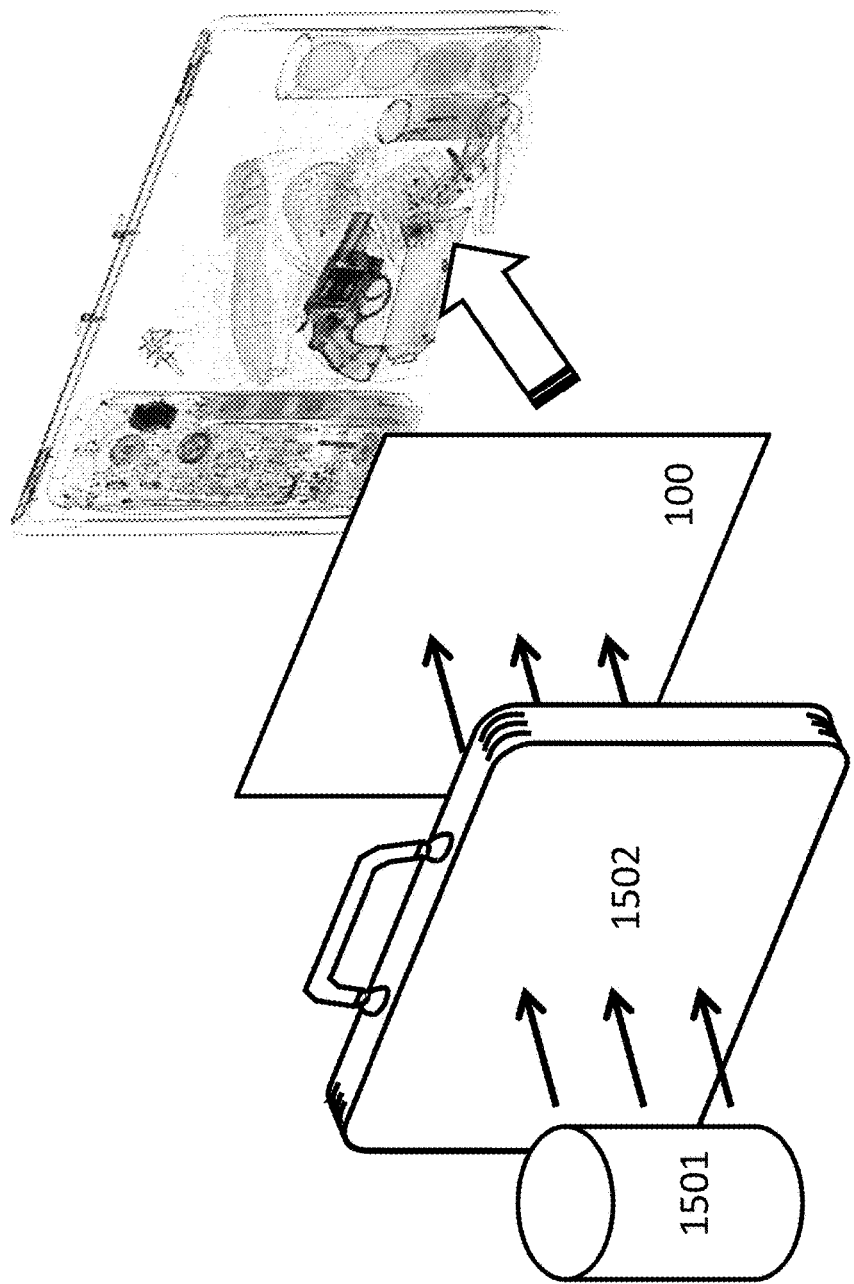
FIG. 16 schematically shows another cargo scanning or non-intrusive inspection (NII) system comprising the semiconductor X-ray detector described herein, according to an embodiment.

FIG. 16 schematically shows another cargo scanning or non-intrusive inspection (NII) system comprising the semiconductor X-ray detector 100 described herein. The system may be used for luggage screening at public transportation stations and airports. The system comprises an X-ray source 1501. X-ray emitted from the X-ray source 1501 may penetrate a piece of luggage 1502, be differently attenuated by the contents of the luggage, and projected to the semiconductor X-ray detector 100. The semiconductor X-ray detector 100 forms an image by detecting the intensity distribution of the transmitted X-ray. The system may reveal contents of luggage and identify items forbidden on public transportation, such as firearms, narcotics, edged weapons, flammables.

Figure 17:
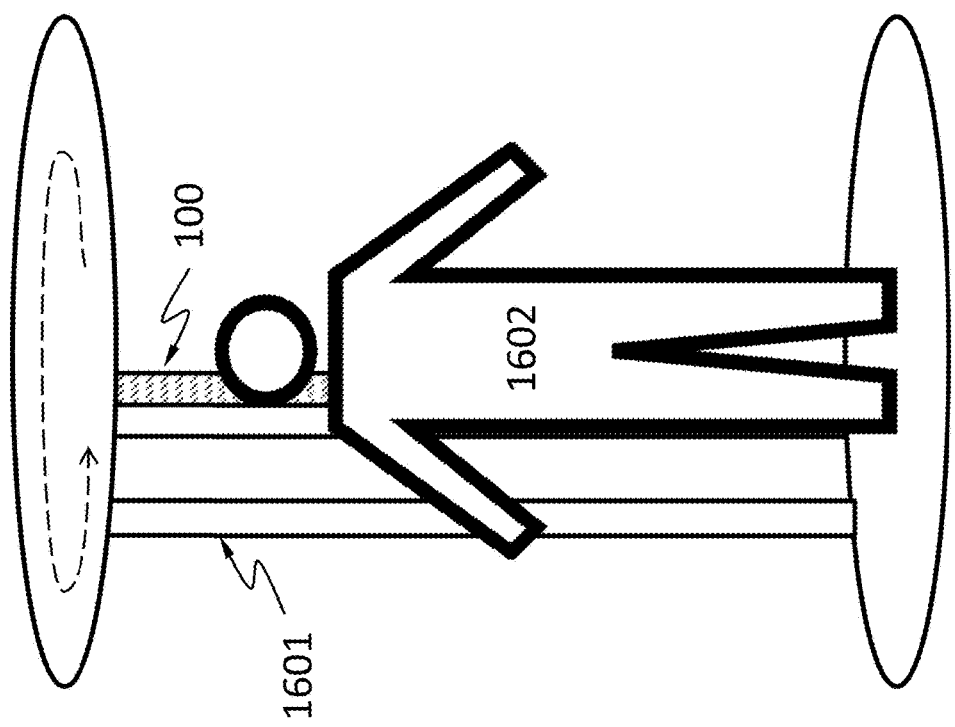
FIG. 17 schematically shows a full-body scanner system comprising the semiconductor X-ray detector described herein, according to an embodiment.

FIG. 17 schematically shows a full-body scanner system comprising the semiconductor X-ray detector 100 described herein. The full-body scanner system may detect objects on a person's body for security screening purposes, without physically removing clothes or making physical contact. The full-body scanner system may be able to detect non-metal objects. The full-body scanner system comprises an X-ray source 1601. X-ray emitted from the X-ray source 1601 may backscatter from a human 1602 being screened and objects thereon, and be projected to the semiconductor X-ray detector 100. The objects and the human body may backscatter X-ray differently. The semiconductor X-ray detector 100 forms an image by detecting the intensity distribution of the backscattered X-ray. The semiconductor X-ray detector 100 and the X-ray source 1601 may be configured to scan the human in a linear or rotational direction.

Figure 18:
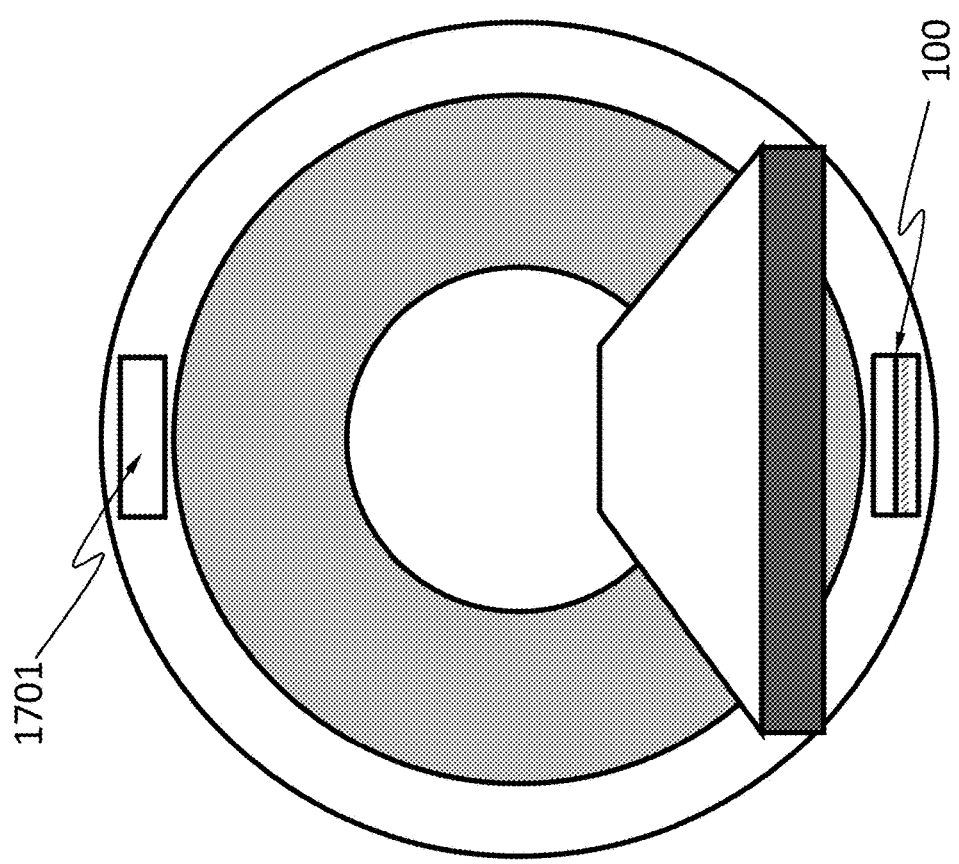
FIG. 18 schematically shows an X-ray computed tomography (X-ray CT) system comprising the semiconductor X-ray detector described herein, according to an embodiment.

FIG. 18 schematically shows an X-ray computed tomography (X-ray CT) system. The X-ray CT system uses computer-processed X-rays to produce tomographic images (virtual "slices") of specific areas of a scanned object. The tomographic images may be used for diagnostic and therapeutic purposes in various medical disciplines, or for flaw detection, failure analysis, metrology, assembly analysis and reverse engineering. The X-ray CT system comprises the semiconductor X-ray detector 100 described herein and an X-ray source 1701. The semiconductor X-ray detector 100 and the X-ray source 1701 may be configured to rotate synchronously along one or more circular or spiral paths.

FIG. 19 schematically shows an electron microscope. The electron microscope comprises an electron source 1801 (also called an electron gun) that is configured to emit electrons. The electron source 1801 may have various emission mechanisms such as thermionic, photocathode, cold emission, or plasmas source. The emitted electrons pass through an electronic optical system 1803, which may be configured to shape, accelerate, or focus the electrons. The electrons then reach a sample 1802 and an image detector may form an image therefrom. The electron microscope may comprise the semiconductor X-ray detector 100 described herein, for performing energy-dispersive X-ray spectroscopy (EDS). EDS is an analytical technique used for the elemental analysis or chemical characterization of a sample. When the electrons incident on a sample, they cause emission of characteristic X-rays from the sample. The incident electrons may excite an electron in an inner shell of an atom in the sample, ejecting it from the shell while creating an electron hole where the electron was. An electron from an outer, higher-energy shell then fills the hole, and the difference in energy between the higher-energy shell and the lower energy shell may be released in the form of an X-ray. The number and energy of the X-rays emitted from the sample can be measured by the semiconductor X-ray detector 100.

The semiconductor X-ray detector 100 described here may have other applications such as in an X-ray telescope, X-ray mammography, industrial X-ray defect detection, X-ray microscopy or microradiography, X-ray casting inspection, X-ray non-destructive testing, X-ray weld inspection, X-ray digital subtraction angiography, etc. It may be suitable to use this semiconductor X-ray detector 100 in place of a photographic plate, a photographic film, a PSP plate, an X-ray image intensifier, a scintillator, or another semiconductor X-ray detector.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. An apparatus suitable for detecting X-ray, comprising:
   an X-ray absorption layer comprising an electrode;
   an electronics layer, the electronics layer comprising: a substrate having a first surface and a second surface, an electronics system in or on the substrate, an electric contact on the first surface, a via, and a transmission line on the second surface;
   wherein the via extends from the first surface to the second surface;
   wherein the electrode is electrically connected to the electric contact;
   wherein the electronics system is electrically connected to the electric contact and the transmission line through the via.

2. The apparatus of claim 1,
   wherein the electronics system comprises:
   a first voltage comparator configured to compare a voltage of the electrode to a first threshold;
   a second voltage comparator configured to compare the voltage to a second threshold;
   a counter configured to register a number of X-ray photons reaching the X-ray absorption layer;
   a controller;
   wherein the controller is configured to start a time delay from a time at which the first voltage comparator determines that an absolute value of the voltage equals or exceeds an absolute value of the first threshold;
   wherein the controller is configured to cause the number registered by the counter to increase by one, if the second voltage comparator determines that an absolute value of the voltage equals or exceeds an absolute value of the second threshold.

3. The apparatus of claim 1, further comprising a capacitor module electrically connected to the electrode, wherein the capacitor module is configured to collect charge carriers from the electrode.

4. The apparatus of claim 2, wherein the controller is configured to activate the second voltage comparator at a beginning or expiration of the time delay.

5. The apparatus of claim 2, further comprising a voltmeter, wherein the controller is configured to cause the voltmeter to measure the voltage upon expiration of the time delay.

6. The apparatus of claim 5, wherein the controller is configured to determine an X-ray photon energy based on a value of the voltage measured upon expiration of the time delay.

7. The apparatus of claim 2, wherein the controller is configured to connect the electrode to an electrical ground.

8. The apparatus of claim 2, wherein a rate of change of the voltage is substantially zero at expiration of the time delay.

9. The apparatus of claim 2, wherein a rate of change of the voltage is substantially non-zero at expiration of the time delay.

10. The apparatus of claim 1, wherein the X-ray absorption layer comprises a diode.

11. The apparatus of claim 1, wherein the X-ray absorption layer comprises silicon, germanium, GaAs, CdTe, CdZnTe, or a combination thereof.

12. The apparatus of claim 1, wherein the apparatus does not comprise a scintillator.

13. The apparatus of claim 1, wherein the apparatus comprises an array of pixels.

14. A system comprising the apparatus of claim 1 and an X-ray source, wherein the system is configured to perform X-ray radiography on human chest or abdomen.

15. A system comprising the apparatus of claim 1 and an X-ray source, wherein the system is configured to perform X-ray radiography on human mouth.

16. A cargo scanning or non-intrusive inspection (NII) system, comprising the apparatus of claim 1 and an X-ray source, wherein the cargo scanning or non-intrusive inspection (NII) system is configured to form an image using backscattered X-ray.

17. A cargo scanning or non-intrusive inspection (NII) system, comprising the apparatus of claim 1 and an X-ray source, wherein the cargo scanning or non-intrusive inspection (NII) system is configured to form an image using X-ray transmitted through an object inspected.

18. A full-body scanner system comprising the apparatus of claim 1 and an X-ray source.

19. An X-ray computed tomography (X-ray CT) system comprising the apparatus of claim 1 and an X-ray source.

20. An electron microscope comprising the apparatus of claim 1, an electron source and an electronic optical system.

21. A system comprising the apparatus of claim 1, wherein the system is an X-ray telescope, or an X-ray microscopy, or wherein the system is configured to perform mammography, industrial defect detection, microradiography, casting inspection, weld inspection, or digital subtraction angiography.

22. The apparatus of claim 2, wherein the controller is configured to deactivate the first voltage comparator at a beginning of the time delay.

23. The apparatus of claim 2, wherein the controller is configured to deactivate the second voltage comparator at expiration of the time delay or at a time when the second voltage comparator determines that the absolute value of the voltage equals or exceeds the absolute value of the second threshold, or a time in between.

24. The apparatus of claim 1, wherein the electronics layer further comprises a peripheral circuit arranged on the first surface.

25. The apparatus of claim 1, wherein the electronics layer further comprises a peripheral circuit arranged between the first surface and the second surface.

26. A system comprising a stack of two layers, each layer comprising a plurality of the apparatuses of claim 1 arranged in an array, wherein the arrays of the two layers are staggered relative to one another.

27. A method comprising:
- obtaining an X-ray absorption layer comprising an electrode;
- obtaining an electronics layer, the electronics layer comprising: a substrate having a first surface and a second surface, an electronics system in or on the substrate, an electric contact on the first surface, a via, and a transmission line on the second surface;
- bonding the X-ray absorption layer and the electronics layer such that the electrode is electrically connected to the electric contact;
- wherein the via extends from the first surface to the second surface;
- wherein the electronics system is electrically connected to the electric contact and the transmission line through the via.

* * * * *